US009637543B2

(12) United States Patent
Zhou et al.

(10) Patent No.: US 9,637,543 B2
(45) Date of Patent: May 2, 2017

(54) HER3 ANTIBODIES AND USES THEREOF

(71) Applicants: THE UAB RESEARCH FOUNDATION, Birmingham, AL (US); BEIJING COTIMES BIOTECH CO., LTD., Beijing (CN)

(72) Inventors: Tong Zhou, Birmingham, AL (US); Donald J. Buchsbaum, Alabaster, AL (US); Enyun Shen, Beijing (CN); Xian Chen, Beijing (CN)

(73) Assignees: THE UAB RESEARCH FOUNDATION, Birmingham, AL (US); BEIJING COTIMES BIOTECH CO., LTD., Beijing (CN)

( * ) Notice: Subject to any disclaimer, the term of this patent is extended or adjusted under 35 U.S.C. 154(b) by 0 days.

(21) Appl. No.: 14/357,524

(22) PCT Filed: Nov. 9, 2012

(86) PCT No.: PCT/US2012/064381
§ 371 (c)(1),
(2) Date: May 9, 2014

(87) PCT Pub. No.: WO2013/071058
PCT Pub. Date: May 16, 2013

(65) Prior Publication Data
US 2014/0314774 A1 Oct. 23, 2014

Related U.S. Application Data

(60) Provisional application No. 61/557,672, filed on Nov. 9, 2011.

(51) Int. Cl.
A61K 39/395 (2006.01)
C07K 16/28 (2006.01)
C07K 16/32 (2006.01)
A61K 31/517 (2006.01)
A61K 45/06 (2006.01)
G01N 33/574 (2006.01)
A61K 39/00 (2006.01)

(52) U.S. Cl.
CPC ........ *C07K 16/2863* (2013.01); *A61K 31/517* (2013.01); *A61K 39/3955* (2013.01); *A61K 45/06* (2013.01); *C07K 16/32* (2013.01); *G01N 33/574* (2013.01); *A61K 2039/505* (2013.01)

(58) Field of Classification Search
None
See application file for complete search history.

(56) References Cited

U.S. PATENT DOCUMENTS

| 2009/0291085 A1 | 11/2009 | Schoeberl et al. | |
| 2010/0183631 A1 | 7/2010 | Rothe et al. | |
| 2013/0224220 A1* | 8/2013 | Muraro | C07K 16/32 424/158.1 |

FOREIGN PATENT DOCUMENTS

| CN | 101674846 | 3/2003 |
| EP | 1283053 | 2/2003 |
| JP | H03502885 | 7/1991 |
| JP | 2002517408 | 6/2002 |
| JP | 2005504044 | 2/2005 |
| JP | 2009514972 | 4/2009 |
| JP | 2009521913 | 6/2009 |
| JP | 2009148282 | 7/2009 |
| JP | 2010518820 | 6/2010 |
| WO | 8906692 | 7/1989 |
| WO | 9962955 | 12/1999 |
| WO | 03013602 | 2/2003 |
| WO | 02100348 | 4/2003 |
| WO | 2007056470 | 5/2007 |
| WO | 2007077028 | 7/2007 |
| WO | 2008100624 | 8/2008 |
| WO | 2010019952 A2 | 2/2010 |
| WO | 2011/022727 | 2/2011 |
| WO | 2012/022814 | 2/2012 |

OTHER PUBLICATIONS

Sala, G. et al., "An ErbB-3 antibody, MP-RM-1, inhibits tumor growth by blocking ligand-dependent and independent activation of ErbB-3/Akt signaling", Oncogene, Aug. 8, 2011, vol. 31, No. 10, pp. 1275-1286.*
Sala et al (Oncogene, 2011, 31:1275-1286; epub Aug. 8, 2011; online pp. 1-12, IDS).*
International Application No. PCT/US2012/064381, International Preliminary Report on Patentability mailed on May 22, 2014, 11 pages.
International Application No. PCT/US2012/064381, International Search Report and Written Opinion mailed on Mar. 20, 2013, 16 pages.
Sala et al., An ErbB-3 antibody, MP-RM-1, inhibits tumor growth by blocking ligand-dependent and independent activation of ErbB-3/Akt signaling, Oncogene, vol. 31, No. 10, Aug. 8, 2011, pp. 1275-1286.
Extended European Search Report for EP Application No. 12847223.0 mailed Oct. 16, 2015, 9 pages.
Chinese Patent Application No. 201280064525.0 , "Office Action", Nov. 4, 2015, 7 pages.
English translation of rejections in Office Action issued on Nov. 4, 2015 for Chinese Patent Application No. 201280064525.0, 2 pages.
Australian Application No. 2012335543, "Examination Report" mailed Sep. 13, 2016.
Chinese Patent Application No. 201280064525.0, "Second Office Action" mailed Sep. 18, 2016.
Partial Supplementary European Search Report for EP Application No. 12847223.0 mailed Jul. 15, 2015.
Japanese Application No. 2014-541312, First Office Action, mailed Aug. 19, 2016.
European Application No. 12 847 223.0 "Examination Report" mailed Dec. 8, 2016, 7 pages.

* cited by examiner

*Primary Examiner* — Laura B Goddard
(74) *Attorney, Agent, or Firm* — Kilpatrick Townsend & Stockton LLP

(57) ABSTRACT

Provided herein are antibodies specific for HER3. Also provided are methods of treating cancer in a subject comprising administering an effective amount of the antibodies described herein to the subject.

17 Claims, 29 Drawing Sheets

SEQUENCE LISTING

```
<160> NUMBER OF SEQ ID NOS: 36

<210> SEQ ID NO 1
<211> LENGTH: 139
<212> TYPE: PRT
<213> ORGANISM: Artificial Sequence
<220> FEATURE:
<223> OTHER INFORMATION: Synthetic construct

<400> SEQUENCE: 1

Met Glu Trp Ile Trp Ile Phe Leu Phe Ile Phe Ser Gly Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Asp Asn Tyr Ile Asn Trp Met Lys Gln Arg Pro Gly Gln Gly Leu
    50                  55                  60

Glu Trp Ile Gly Glu Ile Tyr Pro Gly Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Glu Ser Ala Val
            100                 105                 110

Tyr Phe Cys Ala Arg Ser Pro Asn Leu Arg Leu Tyr Tyr Phe Asp Tyr
        115                 120                 125

Trp Gly Gln Gly Thr Thr Leu Thr Val Ser Ser
    130                 135

<210> SEQ ID NO 2
<211> LENGTH: 127
<212> TYPE: PRT
<213> ORGANISM: Artificial Sequence
<220> FEATURE:
<223> OTHER INFORMATION: Synthetic construct

<400> SEQUENCE: 2

Met Val Ser Thr Ser Gln Leu Leu Gly Leu Leu Leu Phe Trp Thr Ser
1               5                   10                  15

Ala Ser Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Asn Asp Tyr Leu Tyr Trp Tyr Gln Gln Lys Leu His Glu Ser Pro
    50                  55                  60

Arg Leu Leu Ile Lys Phe Ala Ser His Ser Ile Ser Gly Ile Pro Ser
```

```
            65                  70                  75                  80
Arg Phe Ser Gly Ser Gly Ser Gly Ser Asp Phe Thr Leu Ser Ile Asn
                    85                  90                  95
Ser Val Glu Pro Glu Asp Val Gly Val Tyr Tyr Cys Gln Asn Gly His
                    100                 105                 110
Ser Phe Pro Leu Thr Phe Gly Ala Gly Thr Lys Leu Glu Leu Lys
                115                 120                 125
```

<210> SEQ ID NO 3
<211> LENGTH: 11
<212> TYPE: PRT
<213> ORGANISM: Artificial Sequence
<220> FEATURE:
<223> OTHER INFORMATION: Synthetic construct

<400> SEQUENCE: 3

```
Arg Ala Ser Gln Ser Ile Asn Asp Tyr Leu Tyr
1               5                   10
```

<210> SEQ ID NO 4
<211> LENGTH: 7
<212> TYPE: PRT
<213> ORGANISM: Artificial Sequence
<220> FEATURE:
<223> OTHER INFORMATION: Synthetic construct

<400> SEQUENCE: 4

```
Phe Ala Ser His Ser Ile Ser
1               5
```

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

```
Gln Asn Gly His Ser Phe Pro Leu Thr
1               5
```

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

```
Asp Asn Tyr Ile Asn
1               5
```

<210> SEQ ID NO 7
<211> LENGTH: 17
<212> TYPE: PRT
<213> ORGANISM: Artificial Sequence
<220> FEATURE:
<223> OTHER INFORMATION: Synthetic construct

<400> SEQUENCE: 7

```
Glu Ile Tyr Pro Gly Ser Gly Asn Thr Tyr Tyr Asn Glu Lys Phe Lys
1               5                   10                  15
Gly
```

-continued

<210> SEQ ID NO 8
<211> LENGTH: 11
<212> TYPE: PRT
<213> ORGANISM: Artificial Sequence
<220> FEATURE:
<223> OTHER INFORMATION: Synthetic construct

<400> SEQUENCE: 8

Ser Pro Asn Leu Arg Leu Tyr Tyr Phe Asp Tyr
1               5                   10

<210> SEQ ID NO 9
<211> LENGTH: 131
<212> TYPE: PRT
<213> ORGANISM: Artificial Sequence
<220> FEATURE:
<223> OTHER INFORMATION: Synthetic construct

<400> SEQUENCE: 9

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met Asn Trp Tyr Gln Gln Lys Pro
    50                  55                  60

Gly Gln Pro Pro Lys Val Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Thr Pro Val Glu Ala Asp Asp Val Ala Thr Tyr Tyr Cys
            100                 105                 110

Gln Gln Ser Tyr Glu Asp Pro Pro Thr Phe Gly Gly Gly Thr Lys Leu
        115                 120                 125

Glu Ile Lys
    130

<210> SEQ ID NO 10
<211> LENGTH: 136
<212> TYPE: PRT
<213> ORGANISM: Artificial Sequence
<220> FEATURE:
<223> OTHER INFORMATION: Synthetic construct

<400> SEQUENCE: 10

Met Gly Trp Ser Arg Ile Phe Leu Phe Leu Leu Ser Ile Ile Ala Gly
1               5                   10                  15

Val His Cys Gln Val Gln Leu Gln Gln Ser Gly Pro Glu Leu Val Lys
            20                  25                  30

Pro Gly Ala Ser Val Arg Ile Ser Cys Lys Ala Ser Gly Tyr Thr Phe
        35                  40                  45

Thr Asn Tyr Phe Leu His Trp Met Lys Gln Arg Pro Gly Gln Gly Leu
    50                  55                  60

Glu Trp Ile Gly Trp Ile Tyr Pro Gly Asn Val Asn Thr Lys Tyr Ser
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

```
Tyr Phe Cys Ala Arg Ser Thr Tyr Tyr Ser Met Asp Tyr Trp Gly Gln
        115                 120                 125

Gly Thr Ser Val Thr Val Ser Ser
    130                 135

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11

Arg Ala Ser Glu Ser Val Asp Ser Tyr Gly Asn Ser Phe Met Asn
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic construct

<400> SEQUENCE: 12

Arg Ala Ser Asn Leu Glu Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Gln Gln Ser Tyr Glu Asp Pro Pro Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic construct

<400> SEQUENCE: 14

Asn Tyr Phe Leu His
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic construct

<400> SEQUENCE: 15

Trp Ile Tyr Pro Gly Asn Val Asn Thr Lys Tyr Ser Glu Lys Phe Lys
1               5                   10                  15

Gly

<210> SEQ ID NO 16
<211> LENGTH: 8
<212> TYPE: PRT
<213> ORGANISM: Artificial Sequence
```

```
<220> FEATURE:
<223> OTHER INFORMATION: Synthetic construct

<400> SEQUENCE: 16

Ser Thr Tyr Tyr Ser Met Asp Tyr
1               5

<210> SEQ ID NO 17
<211> LENGTH: 20
<212> TYPE: PRT
<213> ORGANISM: Artificial Sequence
<220> FEATURE:
<223> OTHER INFORMATION: Synthetic construct

<400> SEQUENCE: 17

Met Val Ser Thr Ser Gln Leu Leu Gly Leu Leu Leu Phe Trp Thr Ser
1               5                   10                  15

Ala Ser Arg Cys
            20

<210> SEQ ID NO 18
<211> LENGTH: 23
<212> TYPE: PRT
<213> ORGANISM: Artificial Sequence
<220> FEATURE:
<223> OTHER INFORMATION: Synthetic construct

<400> SEQUENCE: 18

Asp Ile Val Met Thr Gln Ser Pro Ala Thr Leu Ser Val Thr Pro Gly
1               5                   10                  15

Asp Arg Val Ser Leu Ser Cys
            20

<210> SEQ ID NO 19
<211> LENGTH: 15
<212> TYPE: PRT
<213> ORGANISM: Artificial Sequence
<220> FEATURE:
<223> OTHER INFORMATION: Synthetic construct

<400> SEQUENCE: 19

Trp Tyr Gln Gln Lys Leu His Glu Ser Pro Arg Leu Leu Ile Lys
1               5                   10                  15

<210> SEQ ID NO 20
<211> LENGTH: 32
<212> TYPE: PRT
<213> ORGANISM: Artificial Sequence
<220> FEATURE:
<223> OTHER INFORMATION: Synthetic construct

<400> SEQUENCE: 20

Gly Ile Pro Ser Arg Phe Ser Gly Ser Gly Ser Gly Ser Asp Phe Thr
1               5                   10                  15

Leu Ser Ile Asn Ser Val Glu Pro Glu Asp Val Gly Val Tyr Tyr Cys
            20                  25                  30

<210> SEQ ID NO 21
<211> LENGTH: 10
<212> TYPE: PRT
<213> ORGANISM: Artificial Sequence
<220> FEATURE:
<223> OTHER INFORMATION: Synthetic construct

<400> SEQUENCE: 21
```

Phe Gly Ala Gly Thr Lys Leu Glu Leu Lys
1               5                   10

<210> SEQ ID NO 22
<211> LENGTH: 19
<212> TYPE: PRT
<213> ORGANISM: Artificial Sequence
<220> FEATURE:
<223> OTHER INFORMATION: Synthetic construct

<400> SEQUENCE: 22

Met Glu Trp Ile Trp Ile Phe Leu Phe Ile Phe Ser Gly Thr Ala Gly
1               5                   10                  15

Val His Ser

<210> SEQ ID NO 23
<211> LENGTH: 30
<212> TYPE: PRT
<213> ORGANISM: Artificial Sequence
<220> FEATURE:
<223> OTHER INFORMATION: Synthetic construct

<400> SEQUENCE: 23

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr
            20                  25                  30

<210> SEQ ID NO 24
<211> LENGTH: 14
<212> TYPE: PRT
<213> ORGANISM: Artificial Sequence
<220> FEATURE:
<223> OTHER INFORMATION: Synthetic construct

<400> SEQUENCE: 24

Trp Met Lys Gln Arg Pro Gly Gln Gly Leu Glu Trp Ile Gly
1               5                   10

<210> SEQ ID NO 25
<211> LENGTH: 32
<212> TYPE: PRT
<213> ORGANISM: Artificial Sequence
<220> FEATURE:
<223> OTHER INFORMATION: Synthetic construct

<400> SEQUENCE: 25

Lys Ala Thr Leu Thr Ala Asp Lys Ser Ser Thr Ala Tyr Met Gln
1               5                   10                  15

Leu Ser Ser Leu Thr Ser Glu Glu Ser Ala Val Tyr Phe Cys Ala Arg
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: Synthetic construct

<400> SEQUENCE: 26

Trp Gly Gln Gly Thr Thr Leu Thr Val Ser Ser
1               5                   10

<210> SEQ ID NO 27
<211> LENGTH: 20

```
<212> TYPE: PRT
<213> ORGANISM: Artificial Sequence
<220> FEATURE:
<223> OTHER INFORMATION: Synthetic construct

<400> SEQUENCE: 27

Met Glu Thr Asp Thr Leu Leu Leu Trp Val Leu Leu Leu Trp Val Pro
1               5                   10                  15

Gly Ser Thr Gly
            20

<210> SEQ ID NO 28
<211> LENGTH: 23
<212> TYPE: PRT
<213> ORGANISM: Artificial Sequence
<220> FEATURE:
<223> OTHER INFORMATION: Synthetic construct

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

Trp Tyr Gln Gln Lys Pro Gly Gln Pro Pro Lys Val Leu Ile Tyr
1               5                   10                  15

<210> SEQ ID NO 30
<211> LENGTH: 32
<212> TYPE: PRT
<213> ORGANISM: Artificial Sequence
<220> FEATURE:
<223> OTHER INFORMATION: Synthetic construct

<400> SEQUENCE: 30

Gly Ile Pro Ala Arg Phe Ser Gly Ser Gly Ser Arg Thr Asp Phe Thr
1               5                   10                  15

Leu Thr Ile Thr Pro Val Glu Ala Asp Asp Val Ala Thr Tyr Tyr Cys
            20                  25                  30

<210> SEQ ID NO 31
<211> LENGTH: 10
<212> TYPE: PRT
<213> ORGANISM: Artificial Sequence
<220> FEATURE:
<223> OTHER INFORMATION: Synthetic construct

<400> SEQUENCE: 31

Phe Gly Gly Gly Thr Lys Leu Glu Ile Lys
1               5                   10

<210> SEQ ID NO 32
<211> LENGTH: 19
<212> TYPE: PRT
<213> ORGANISM: Artificial Sequence
<220> FEATURE:
<223> OTHER INFORMATION: Synthetic construct
```

```
<400> SEQUENCE: 32

Met Gly Trp Ser Arg Ile Phe Leu Phe Leu Leu Ser Ile Ile Ala Gly
1               5                   10                  15

Val His Cys

<210> SEQ ID NO 33
<211> LENGTH: 30
<212> TYPE: PRT
<213> ORGANISM: Artificial Sequence
<220> FEATURE:
<223> OTHER INFORMATION: Synthetic construct

<400> SEQUENCE: 33

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr
            20                  25                  30

<210> SEQ ID NO 34
<211> LENGTH: 14
<212> TYPE: PRT
<213> ORGANISM: Artificial Sequence
<220> FEATURE:
<223> OTHER INFORMATION: Synthetic construct

<400> SEQUENCE: 34

Trp Met Lys Gln Arg Pro Gly Gln Gly Leu Glu Trp Ile Gly
1               5                   10

<210> SEQ ID NO 35
<211> LENGTH: 32
<212> TYPE: PRT
<213> ORGANISM: Artificial Sequence
<220> FEATURE:
<223> OTHER INFORMATION: Synthetic construct

<400> SEQUENCE: 35

Lys Ala Thr Leu Thr Ala Asp Lys Ser Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 36
<211> LENGTH: 11
<212> TYPE: PRT
<213> ORGANISM: Artificial Sequence
<220> FEATURE:
<223> OTHER INFORMATION: Synthetic construct

<400> SEQUENCE: 36

Trp Gly Gln Gly Thr Ser Val Thr Val Ser Ser
1               5                   10
```

HER3 ANTIBODIES AND USES THEREOF

CROSS-REFERENCE TO PRIORITY APPLICATION

This application claims priority to U.S. Provisional Application No. 61/557,672 filed Nov. 9, 2011, which is incorporated herein by reference in its entirety.

STATEMENT REGARDING FEDERALLY FUNDED RESEARCH

This invention was made with government funding under Grant No. RO1-CA112169 from the National Institutes of Health. The government has certain rights in this invention.

BACKGROUND

HER3, also known as ERBB3, is a member of the ErbB protein family. The ErbB protein family consists of four closely related transmembrane tyrosine kinase receptors, epidermal growth factor receptor (EGFR) (also known as HER1), ERBB2 (HER2), ERBB3 (HER3), and ERBB4 (HER4). Each receptor comprises an extracellular domain, an α-helical transmembrane segment and an intracellular tyrosine kinase domain. Dimerization of the receptors is an essential requirement for receptor function. Different heterodimers can form between the ErbB receptor protein family, and which heterodimers are formed and which ligands are bound determines which signaling pathways are activated.

SUMMARY

Provided herein are antibodies or fragments thereof specific for HER3, wherein the antibodies or fragments block phosphorylation of HER3 (either autophosphorylation and/or ligand-induced phosphorylation). Certain antibodies or fragments provided herein specifically bind HER3 and do not block HER3 ligand binding, whereas others specifically bind HER3 but block ligand binding. Antibodies or fragments described herein that do not block ligand binding are referred to herein as ligand-independent antibodies or fragments because autophosphorylation is blocked. Antibodies or fragments described herein that do block ligand binding are referred to herein as ligand-dependent antibodies or fragments because ligand-induced phosphorylation is blocked.

Also provided herein are methods of treating proliferative disorders (e.g., cancer) in a subject. The methods comprise administering to the subject an effective amount of the antibodies or fragments thereof described herein. For example, provided is a method comprising administering to the subject a combination of a ligand-independent antibody or fragment thereof and a ligand-dependent antibody or fragment thereof, optionally in combination with other antibodies or fragments.

The details of one or more embodiments are set forth in the accompanying drawings and the description below. Other features, objects, and advantages will be apparent from the description and drawings, and from the claims.

DESCRIPTION OF DRAWINGS

FIG. 1 shows the specific binding of the 1A5 and 3D4 antibodies to HER3.

FIG. 2 shows the effect of the 1A5 and 3D4 antibodies on ligand binding to HER3.

FIG. 17 shows the expression and function of ERBB family proteins in pancreatic cancer cell lines.

FIG. 18 shows the effect of the 1A5 antibody, erlotinib and lapatinib on ligand-independent activation of ERBB family proteins.

FIG. 19 shows the effect of the 3D4 antibody, erlotinib and lapatinib on ligand-dependent activation of ERBB family proteins.

FIG. 20 shows the anti-proliferation activity of a combination treatment with anti-HER3 antibodies and erlotinib or lapatinib.

DETAILED DESCRIPTION

Figure 1A:
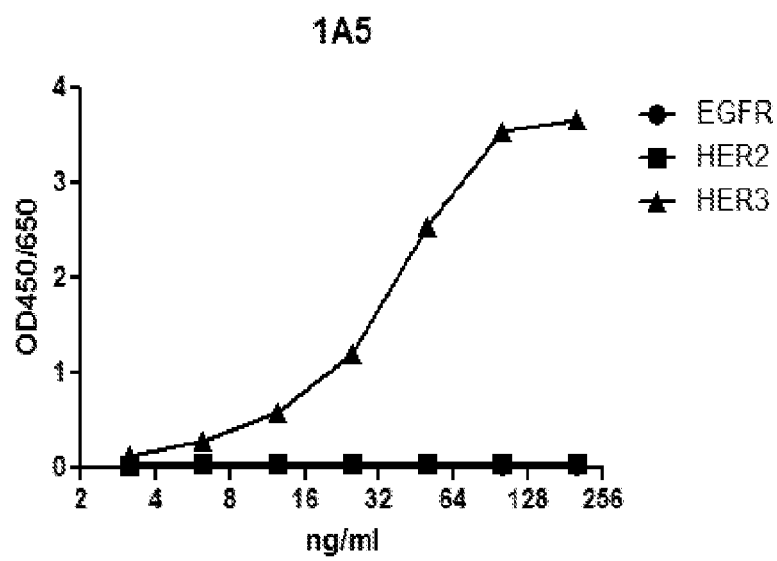
FIGS. 1A and 1B show graphs demonstrating the binding specificity of 1A5 (FIG. 1A) and 3D4 (FIG. 1B) as determined by an ELISA assay. The ELISA plate was coated with 1 μg/ml of recombinant soluble EGFR, HER2, or HER3 (extracellular domain) and incubated with the indicated concentrations of 1A5 or 3D4, followed by HRP-goat anti-mouse IgG. The average OD values of triplicates are presented. The values for egFR are superimposed on the values for HER2.

Provided herein are antibodies or fragments thereof specific for HER3. The antibodies block phosphorylation of HER3. The blocked phosphorylation can be autophosphorylation or ligand-induced phosphorylation. Optionally, the HER3 antibodies do not block HER3 ligand binding. As used herein, an antibody or fragment that does not block HER3 ligand binding is referred to as a ligand-independent antagonistic antibody or fragment thereof because autophosphorylation is blocked. Optionally, the HER3 antibodies block HER3 ligand binding. As used herein, an antibody or fragment that blocks HER3 ligand binding is referred to as a ligand-dependent antagonistic antibody or fragment because ligand-induced phosphorylation is blocked. The HER3 specific antibodies block phosphorylation of HER3, and, optionally, the phosphorylation of HER3 is independent of HER3 ligand binding. The antibodies can, for example, sensitize blockade of phosphorylation of HER2 and EGFR by agents that block ligand-induced phosphorylation of HER2 and EGFR.

Optionally, the HER3 specific antibodies or fragments can block phosphorylation of HER3 in vitro at low doses in a cancer cell expressing HER3. Optionally, a ligand-independent and a ligand-dependent HER3 specific antibody or fragment can be administered in combination, in vitro, at low doses, to a cancer cell expressing HER3. The dosage of HER3 specific antibodies can, for example, be 0.1 µg/ml, 0.5 µg/ml, 1 µg/ml, 2.5 µg/ml, 5 µg/ml, 10 µg/ml, 20 µg/ml, 50 µg/ml, or any dose in between. The cancer cell can, for example, be selected from the group consisting of a gastric cancer cell, a breast cancer cell, a pancreatic cancer cell, a prostate cancer cell, an ovarian cancer cell, a neural cancer cell, a liver cancer cell, a kidney cancer cell, a skin cancer cell, a colorectal cancer cell, and a lung cancer cell.

A ligand-independent HER3 specific antibody or fragment can, for example, have the same epitope specificity as an antibody or fragment with a light chain with polypeptide sequences (complementarity determining regions or CDRS) comprising SEQ ID NO:3, SEQ ID NO:4, and SEQ ID NO:5 and a heavy chain with polypeptide sequences (CDRS) comprising SEQ ID NO:6, SEQ ID NO:7, and SEQ ID NO:8. Optionally, the antibody or fragment comprises a light chain comprising SEQ ID NO: 2. Optionally, the antibody or fragment comprises a heavy chain comprising SEQ ID NO: 1. The light chain can, for example, comprise polypeptide sequences (CDRS) comprising SEQ ID NO:3, SEQ ID NO:4, and SEQ ID NO:5. The heavy chain can, for example, comprise polypeptide sequences (CDRS) comprising SEQ ID NO:6, SEQ ID NO:7, and SEQ ID NO:8.

A ligand-dependent HER3 specific antibody or fragment can, for example, have the same epitope specificity as an antibody or fragment with a light chain with polypeptide sequences (CDRS) comprising SEQ ID NO:11, SEQ ID NO:12, and SEQ ID NO:13 and a heavy chain with polypeptide sequences (CDRS) comprising SEQ ID NO:14, SEQ ID NO:15, and SEQ ID NO:16. Optionally, the antibody or fragment comprises a light chain comprising SEQ ID NO:9. Optionally, the antibody or fragment comprises a heavy chain comprising SEQ ID NO:10. The light chain can, for example, comprise polypeptide sequences (CDRS) comprising SEQ ID NO:11, SEQ ID NO:12, and SEQ ID NO:13. The heavy chain can, for example, comprise polypeptide sequences (CDRS) comprising SEQ ID NO:14, SEQ ID NO:15, and SEQ ID NO:16.

As used herein, the term antibody encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term variable is used herein to describe certain portions of the antibody domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

As used herein, the term epitope is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics. Identification of the epitope that the antibody recognizes is performed as follows. First, various partial structures of the target molecule that the monoclonal antibody recognizes are prepared. The partial structures are prepared by preparing partial peptides of the molecule. Such peptides are prepared by, for example, known oligopeptide synthesis technique or by incorporating DNA encoding the desired partial polypeptide in a suitable expression plasmid. The expression plasmid is delivered to a suitable host, such as E. coli, to produce the peptides. For example, a series of polypeptides having appropriately reduced lengths, working from the C- or N-terminus of the target molecule, can be prepared by established genetic engineering techniques. By establishing which fragments react with the antibody, the epitope region is identified. The epitope is more closely identified by synthesizing a variety of smaller peptides or mutants of the peptides using established oligopeptide synthesis techniques. The smaller peptides are used, for example, in a competitive inhibition assay to determine whether a specific peptide interferes with binding of the antibody to the target molecule. If so, the peptide is the epitope to which the antibody binds. Commercially available kits, such as the SPOTs Kit (Genosys Biotechnologies, Inc., The Woodlands, Tex.) and a series of multipin peptide synthesis kits based on the multipin synthesis method (Chiron Corporation, Emeryvile, Calif.) may be used to obtain a large variety of oligopeptides.

The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain HER3 binding activity are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies: A Laboratory Manual, Cold Spring Harbor Publications, New York (1988)).

Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies: A Laboratory Manual, Cold Spring Harbor Publications, New York (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent can be HER3 or an immunogenic fragment thereof.

Generally, either peripheral blood lymphocytes (PBLs) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") substances that prevent the growth of HGPRT-deficient cells.

Immortalized cell lines useful here are those that fuse efficiently, support stable high level expression of antibody by the selected antibody-producing cells, and are sensitive to a medium such as HAT medium. Immortalized cell lines include murine myeloma lines, which can be obtained, for instance, from the Salk Institute Cell Distribution Center; San Diego, Calif. and the American Type Culture Collection; Rockville, Md. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York (1987) pp. 51-63).

The culture medium in which the hybridoma cells are cultured can then be assayed for the presence of monoclonal antibodies directed against HER3 or selected epitopes thereof. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in Harlow and Lane Antibodies, A Laboratory Manual, Cold Spring Harbor Publications, New York (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816, 567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for HER3 and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or fragments is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied Biosystems, Inc.; Foster City, Calif.). Those of skill in the art readily appreciate that a peptide or polypeptide corresponding to the antibody provided herein, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer Verlag Inc., NY). Alternatively, the peptide or polypeptide can by independently synthesized in vivo. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

The provided fragments or antibody polypeptides can be recombinant proteins obtained by cloning nucleic acids encoding the polypeptide in an expression system capable of producing the polypeptide fragments thereof, such as a bacterial, adenovirus or baculovirus expression system. For example, one can determine the active domain of an antibody from a specific hybridoma that can cause a biological effect associated with the interaction of the antibody with HER3. For example, amino acids found to not contribute to either the activity or the binding specificity or affinity of the antibody can be deleted without a loss in the respective activity.

The provided fragments, whether attached to other sequences, can also include insertions, deletions, substitutions, or other selected modifications of particular regions or specific amino acids residues, provided the activity of the fragment is not significantly altered or impaired compared to the nonmodified antibody or epitope. These modifications can provide for some additional property, such as to remove or add amino acids capable of disulfide bonding, to increase its bio longevity, to alter its secretory characteristics, and the like. In any case, the fragment can possess a bioactive property, such as binding activity, regulation of binding at the binding domain, and the like. Functional or active regions may be identified by mutagenesis of a specific region of the protein, followed by expression and testing of the expressed polypeptide. Such methods are readily apparent to a skilled practitioner in the art and can include site specific mutagenesis of the nucleic acid encoding the antigen. (Zoller et al., Nucl. Acids Res. 10:6487-500 (1982)).

Further provided herein is a humanized or human version of the antibody. Optionally, the antibody modulates the activity of the HER3 molecule by inhibiting the activation of the HER3 molecule. Optionally, the humanized or human antibody comprises at least one complementarity determining region (CDR) of an antibody having the same epitope specificity as an antibody produced by a disclosed hybridoma cell line. For example, the antibody can comprise all CDRs of an antibody having the same epitope specificity as an antibody produced by the hybridoma cell line.

Optionally, the humanized or human antibody can comprise at least one residue of the framework region of the monoclonal antibody produced by a disclosed hybridoma cell line. Humanized and human antibodies can be made using methods known to a skilled artesian; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind HER3. See, e.g., Lonberg and Huszar, Int. Rev. Immunol. 13:65-93, (1995), which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human.

Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321:522-525 (1986); Riechmann et al., Nature 332:323-327 (1988); or Verhoeyen et al., Science 239:1534-1536 (1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The nucleotide sequences encoding the provided antibodies can be readily isolated and sequenced using conventional procedures (e.g., by using oligonucleotide probes that are capable of binding specifically to genes encoding the heavy and light chains of murine antibodies). These nucleotide sequences can also be modified, or humanized, for example, by substituting the coding sequence for human heavy and light chain constant domains in place of the homologous murine sequences (see, e.g., U.S. Pat. No. 4,816,567). The nucleotide sequences encoding any of the provided antibodies can be expressed in appropriate host cells. These include prokaryotic host cells including, but not limited to, *E. coli, Bacillus subtilus*, other enterobacteriaceae such as *Salmonella typhimurium* or *Serratia marcesans*, and various *Pseudomonas* species. Eukaryotic host cells can also be utilized. These include, but are not limited to, yeast cells (for example, *Saccharomyces cerevisiae* and *Pichia pastoris*), and mammalian cells such as VERO cells, HeLa cells, Chinese hamster ovary (CHO) cells, W138 cells, BHK cells, COS-7 cells, 293T cells and MDCK cells. The antibodies produced by these cells can be purified from the culture medium and assayed for binding, activity, specificity or any other property of the monoclonal antibodies by utilizing the methods set forth herein and standard in the art.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA 90:2551-5 (1993); Jakobovits et al., Nature 362:255-8 (1993); Bruggemann et al., Year in Immuno. 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, ed., p. 77 (1985); Boerner et al., J. Immunol., 147(1):86-95 (1991)).

The provided antibody or fragment can be labeled or fused with another polypeptide or fragment thereof. For example, the provided antibodies or fragments thereof can be fused with a therapeutic agent. Thus, an antibody or fragment thereof that binds to HER3 may be linked to a therapeutic agent. The linkage can be covalent or noncovalent (e.g., ionic). Therapeutic agents include but are not limited to toxins, including but not limited to plant and bacterial toxins, small molecules, peptides, polypeptides and proteins. Genetically engineered fusion proteins, in which genes encoding for an antibody or fragments thereof, including the Fv region, can be fused to the genes encoding a toxin to deliver a toxin to the target cell are also provided. As used herein, a target cell or target cells are HER3 positive cells.

Other examples of therapeutic agents include chemotherapeutic agents (including small molecules), a radiotherapeutic agent, and immunotherapeutic agent, as well as combinations thereof. In this way, the antibody complex delivered to the subject can be multifunctional, in that it exerts one therapeutic effect by binding to the HER3 and a second therapeutic by delivering a supplemental therapeutic agent.

The therapeutic agent can act extracellularly, for example by initiating or affecting an immune response, or it can act intracellularly, either directly by translocating through the cell membrane or indirectly by, for example, affecting transmembrane cell signaling. The therapeutic agent is optionally cleavable from the antibody or fragment. Cleavage can be autolytic, accomplished by proteolysis, or by contacting the cell with a cleavage agent.

Examples of toxins or toxin moieties include diphtheria, ricin, streptavidin, and modifications thereof. An antibody or antibody fragment may be conjugated to a therapeutic moiety such as a cytotoxin, a therapeutic agent or a radioactive metal ion. A cytotoxin or cytotoxic agent includes any agent that is detrimental to cells. Examples include paclitaxel, cisplatin, carboplatin, cytochalasin B, gramicidin D, ethidium bromide, emetine, etoposide, tenoposide, colchicin, dihydroxy anthracin dione, mitoxantrone, mithramycin, actinomycin D, 1-dehydrotestosterone, glucocorticoids, procaine, tetracaine, lidocaine, propranolol, puromycin and analogs or homologs thereof. Therapeutic agents include, but are not limited to, antimetabolites (e.g., methotrexate, 6-mercaptopurine, 6-thioguanine, cytarabine, 5-fluorouracil, decarbazine), alkylating agents (e.g., mechlorethamine, thiotepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e. g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such a therapeutic moiety to antibodies are well known, see, e.g., Arnon et al., Monoclonal Antibodies And Cancer Therapy, Reisfeld et al. (eds.), pp. 243-56 (1985); Hellstrom et al., Controlled Drug Delivery (2nd Ed.), Robinson et al. (eds.), pp. 623-53 (1987); Thorpe, Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy" in Monoclonal Antibodies For Cancer Detection And Therapy, Baldwin et al. (eds.), pp. 303-16 (1985), and Thorpe et al., Immunol. Rev. 62:119-58 (1982). Alternatively, an antibody can be conjugated to a second antibody to form an antibody heteroconjugate as described in U.S. Pat. No. 4,676,980.

Provided herein is a HER3 antibody, a humanized HER3 antibody, heavy and light chain immunoglobulins of a HER3 antibody, CDRs of the HER3 antibody, and certain truncations or fragments of these antibodies or immunoglobulines that perform the functions of the full length antibody or immunoglobulin. For example, the nucleic acid sequence coding for the HER3 antibodies can be altered. As such, nucleic acids that encode the polypeptide sequences, variants, and fragments of thereof are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

As with all peptides, polypeptides, and proteins, including fragments thereof, it is understood that additional modifications in the amino acid sequence of the HER3 antibodies can occur that do not alter the nature or function of the peptides, polypeptides, or proteins. Such modifications include conservative amino acids substitutions and are discussed in greater detail below.

The HER3 antibodies or fragments provided herein have a desired function. The HER3 antibody or fragment binds a specific epitope of the HER3 protein. Binding of the epitope can, for example, inhibit phosphorylation of HER3 (either autophosphorylation or ligand-induced phosphorylation).

The HER3 antibodies or fragments described herein can be further modified and varied so long as the desired function is maintained. It is understood that one way to define any known modifications and derivatives or those that might arise of the disclosed nucleic acid sequences and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the polypeptides of the HER3 antibodies or fragments provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol Biol. 48: 443 (1970), by the search for similarity method of Pearson and Lipman, Proc. Natl. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism), may arise due to environmental influence (e.g., exposure to ultraviolet light), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residues inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Also provided are herein are methods of treating cancer in a subject comprising administering to the subject an effective amount of a ligand-independent HER3 specific antibody or fragment, a ligand-dependent HER3 specific antibody or fragment, or a combination of both. Optionally, the subject is first selected as having a HER3 expressing cancer. The methods can comprise administering to the subject a first ligand-independent or ligand-dependent HER3 specific antibody or fragment, optionally with or followed by administering to the subject a second ligand-dependent HER3 specific antibody or fragment in the event that the first antibody or fragment was a ligand-independent HER3 specific antibody or fragment or a ligand-independent HER3 specific antibody or fragment in the event that the first antibody or fragment was a ligand-dependent HER3 specific antibody or fragment. Optionally, the methods can further comprise administering to the subject an antibody or fragment that blocks phosphorylation to HER2 and/or EGFR.

The methods can, for example, further comprise administering to the subject one or more tyrosine kinase inhibitors. The one or more tyrosine kinase inhibitors can be selected from erlotinib, lapatinib, axitinib, bosutinib, cediranib, dasatinib, gefitinib, imatinib, lestaurtinib, nilotinib, semaxanib, sunitinib, and vandetanib.

When combinations of antibodies or combinations of antibodies and tyrosine kinase inhibitors are administered, the agents can be provided in any order (e.g., simultaneously in the same composition, simultaneously by different compositions or different routes of administration, or sequentially).

Further provided herein is a method of promoting sensitivity to a tyrosine kinase inhibitor or preventing or reducing resistance to a tyrosine kinase inhibitor in a subject. The method comprises administering to the subject an effective amount of a ligand-independent HER3 specific antibody or fragment as disclosed herein, optionally in combination with an effective amount of a ligand-dependent HER3 specific antibody or fragment, as disclosed herein. The method further comprises administering to the subject a tyrosine kinase inhibitor. The tyrosine kinase inhibitor can be administered in a lower dosage than in the absence of the antibody or fragment or antibodies or fragments.

The methods can, for example, further comprise administering to the subject one or more anticancer compounds or chemotherapeutic agents. Chemotherapeutic agents are compounds which can inhibit the growth of tumors. Such agents, include, but are not limited to, antineoplastic agents such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin C; Mitosper; Mitotane; Mitoxantrone; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

When combinations of antibodies or combinations of antibodies and chemotherapeutic agents are administered, the agents can be provided in any order (e.g., simultaneously in the same composition, simultaneously by different compositions or different routes of administration, or sequentially).

Further provided herein is a method of promoting sensitivity to a chemotherapeutic agent or preventing or reducing resistance to a chemotherapeutic agent in a subject. The method comprises administering to the subject an effective amount of a ligand-independent HER3 specific antibody or fragment as disclosed herein, optionally in combination with an effective amount of a ligand-dependent HER3 specific antibody or fragment, as disclosed herein. The method further comprises administering to the subject a chemotherapeutic agent. The chemotherapeutic agent can be administered in a lower dosage than in the absence of the antibody or fragment or antibodies or fragments.

Also provided herein are methods of screening for an agent that blocks ligand-independent phosphorylation of HER3. The methods comprise administering the agent to be tested to a HER3-expressing cell and detecting a level of HER3 phosphorylation. A decreased level of HER3 phosphorylation as compared to an untreated cell indicates that the agent blocks ligand-independent phosphorylation of HER3. The method can further comprise administering a HER3 ligand to the HER3-expressing cell and detecting a level of ligand-dependent phosphorylation and further comparing it to the level of ligand-independent phosphorylation (e.g., to determine if the phosphorylation is ligand-dependent or ligand independent). Optionally, the HER3 ligand is administered prior to administering the agent to be tested. Further provided herein is an agent identified by the methods of screening provided herein.

Provided herein are compositions comprising one or more HER3 antibodies or fragments described herein, optionally, further comprising one or more HER2, EGFR antibodies or fragments thereof, or one or more tyrosine kinase inhibitors. The herein provided compositions are suitable for administration in vitro or in vivo. Optionally, the compositions comprising one or more HER3 antibodies or fragments can further comprise a pharmaceutically acceptable carrier. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in *Remington: The Science and Practice of Pharmacy*, 21$^{st}$ *Edition,* David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the composition, e.g., the polypeptides described herein and the adenovirus encoding an antigen to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, a nucleic acid molecule encoding the HER3 specific antibody or fragment is administered by a vector comprising the nucleic acid molecule. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

As used herein, the term proliferative disorder refers to any cellular disorder in which the cells proliferate more rapidly than normal tissue growth. Proliferative disorders include, for example, cancer, such as, an HER3 expressing cancer, pancreatic cancer, breast cancer, brain cancer (e.g., glioblastoma), lung cancer, prostate cancer, colorectal cancer, thyroid cancer, renal cancer, skin cancer, adrenal cancer, stomach cancer or liver cancer.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the agents described herein are administered to a subject prior to onset (e.g., before obvious signs of cancer) or during early onset (e.g., upon initial signs and symptoms of cancer). Prophylactic administration can occur for several days to years prior to the manifestation of symptoms of cancer. Prophylactic administration can be used, for example, in the preventative treatment of subjects diagnosed with a genetic predisposition to cancer. Therapeutic treatment involves administering to a subject a therapeutically effective amount of the agents described herein after diagnosis or development of cancer.

According to the methods taught herein, the subject is administered an effective amount of the HER3 antibody or fragment thereof. The terms effective amount and effective dosage are used interchangeably. The term effective amount is defined as any amount necessary to produce a desired physiologic response (e.g., a reduction in tumor volume). Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Identification of Ligand-Independent (1A5) and Ligand-Dependent (3D4) HER3 Antibodies In a functional screen of a hybridoma library made against the DR5-apoptosis resistant human breast cancer ZR75-1 cell line, the 1A5 antibody was identified. In the presence of the 1A5 antibody and an agonistic DR5-antibody selected from TRA-8 or CTB006, apoptosis of the DR5-resistant ZR75-1 cells was observed. The target of the 1A5 antibody was identified to be HER3 by immunoprecipitation with the 1A5 antibody and subsequent mass spectrometry analysis.

Another HER3 antibody was generated by immunizing mice with human HER3 expressing SP 2/0 cells. The antibody was identified in a functional screen by its ability to inhibit ligand-induced HER3 activation in human cancer cells lines. Thus, the 3D4 antibody is a ligand-dependent antibody.

Example 2

Figure 1B:
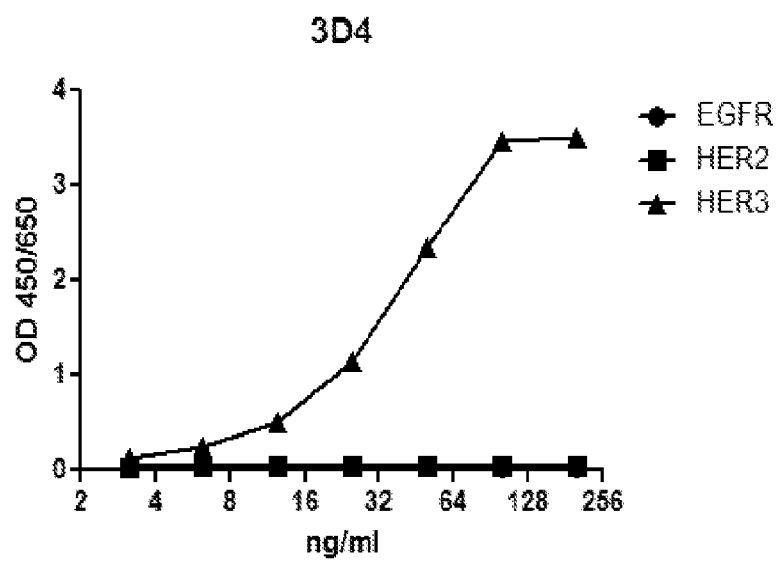
Figure 1C:
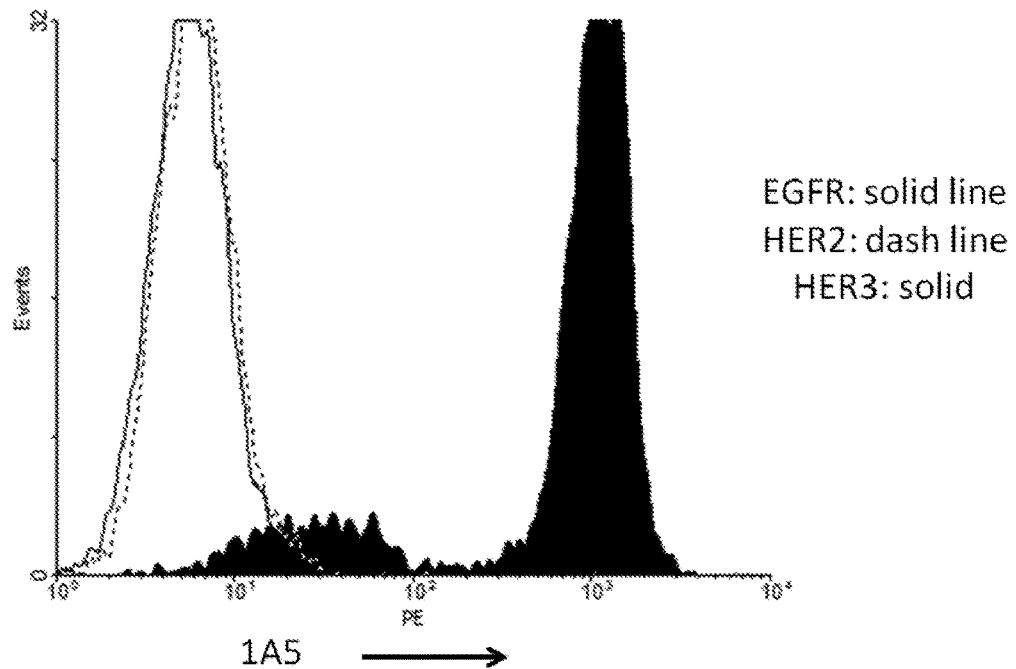
FIGS. 1C and 1D show flow cytometry results demonstrating the binding specificity of 1A5 (FIG. 1C) and 3D4 (FIG. 1D). EGFR, HER2 or HER3-transfected SP 2/0 cells were stained with 1 μg/ml of purified antibody, followed by PE-goat anti-mouse IgG.
Figure 1D:
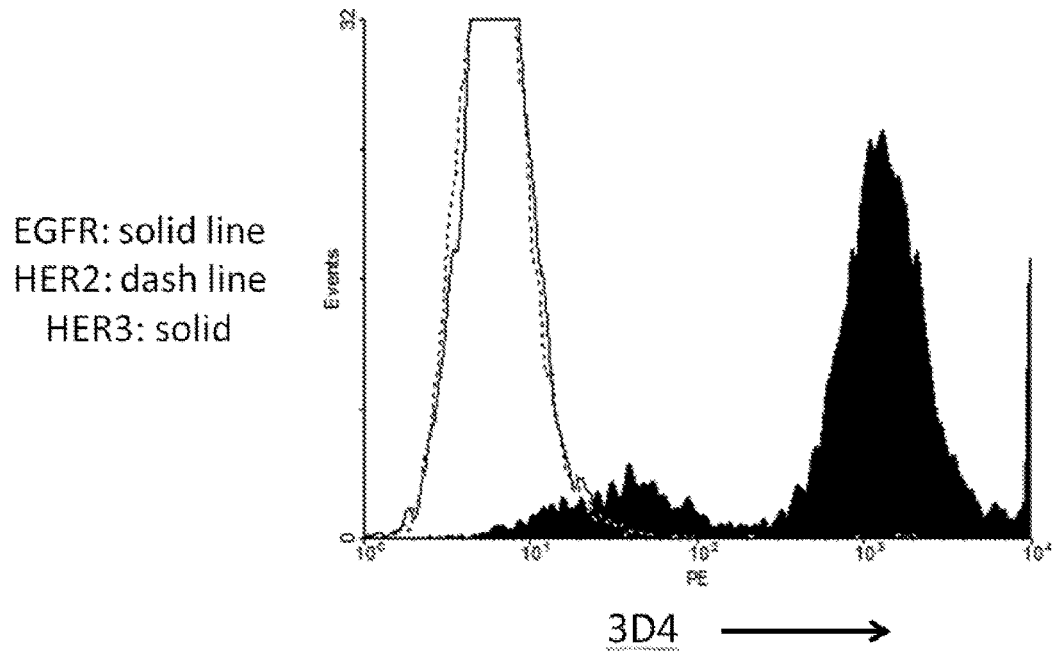

Characterization of Ligand-Independent (1A5) and Ligand-Dependent (3D4) HER3 Antibodies To demonstrate the binding specificity of the 1A5 and 3D4 antibodies, an ELISA assay was performed. An ELISA plate was coated with 1 µg/ml of recombinant soluble EGFR, HER2, or the extracellular domain of HER3. The ELISA plate was incubated with increasing concentrations of 1A5 or 3D4, followed by incubation with a secondary HRP-goat anti-mouse IgG to detect 1A5 and 3D4 antibody binding. It was determined that both the 1A5 and 3D4 antibodies specifically bind HER3 (FIGS. 1A and 1B). As confirmation, the binding specificity of the 1A5 and 3D4 antibodies was also examined by flow cytometry. EGFR, HER2, or HER3 transfected SP2/0 cells were stained with 1 µg/ml of purified 1A5 or 3D4 antibody, followed by a PE-goat anti-mouse IgG to detect 1A5 and 3D4 antibody binding. Using flow cytometry, it was confirmed that the 1A5 and 3D4 antibodies specifically bind HER3 (FIGS. 1C and 1D).

Figure 2A:
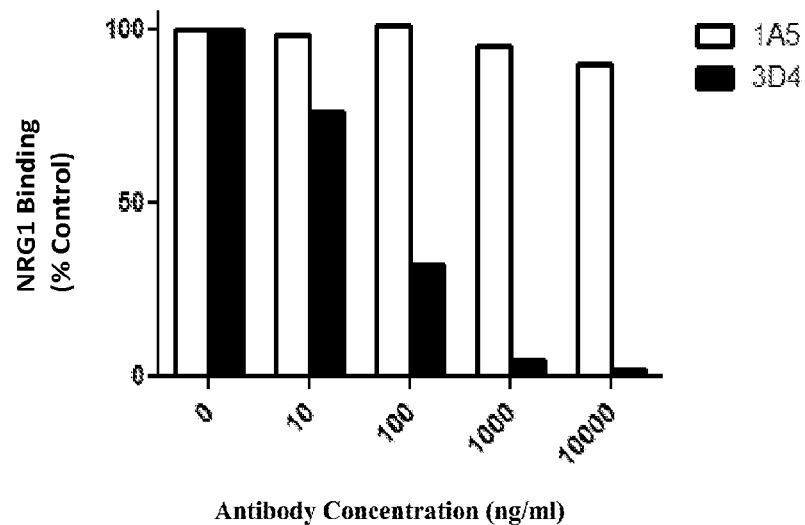
FIG. 2A shows a graph demonstrating that the 1A5 antibody does not block ligand binding to HER3, whereas the 3D4 antibody blocks ligand binding to HER3, as determined by an ELISA assay. The ELISA plate was coated with 1 μg/ml of recombinant soluble HER3 and then incubated with 100 ng/ml of biotin-conjugated recombinant NRG1 in the absence or presence of the indicated concentrations of the 1A5 and 3D4 antibodies. The binding of NRG1 to HER3 (vertical axis) was detected by HRP-streptavidin.
Figure 2B:
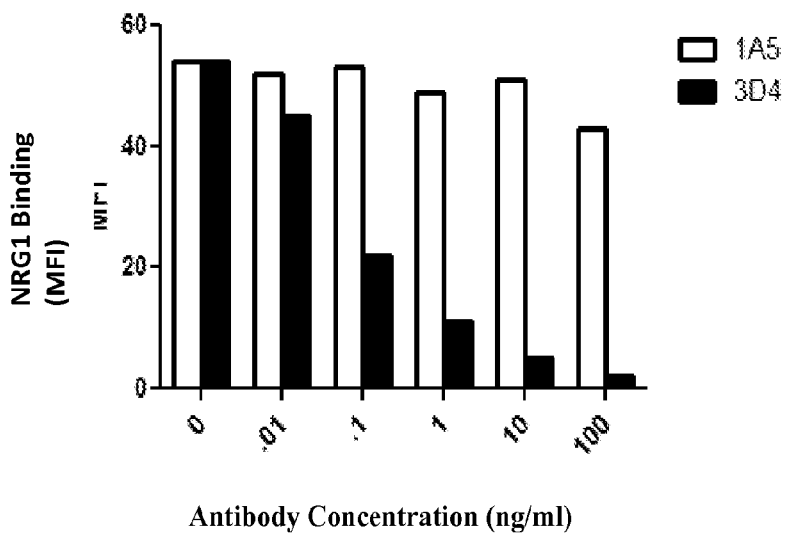
FIG. 2B shows a graph demonstrating that the 1A5 antibody does not block ligand binding to HER3, whereas the 3D4 antibody blocks ligand binding to HER2, as determined by flow cytometry. HER3-transfected SP 2/0 cells were incubated with 100 ng/ml of biotin-conjugated NRG1 in the absence or presence of the indicated concentrations of 1A5 or 3D4 antibodies. NRG1 binding was detected by PE-streptavidin. The mean fluorescent intensities (MFI) of NRG1 bound are presented.

To determine whether the 1A5 and 3D4 antibodies are capable of blocking ligand binding (e.g., NRG1) to HER3, an ELISA assay was performed. An ELISA plate was coated with 1 µg/ml of recombinant soluble HER3 and then incubated with 100 ng/ml of biotin-conjugated recombinant NRG1 in the absence of presence of increasing concentrations of 1A5 or 3D4. The binding of NRG1 to HER3 was detected by HRP-streptavidin. Increasing concentrations of 1A5 antibody failed in block NRG1 binding to HER3 (FIG. 2A) indicating that the 1A5 antibody binds HER3 without blocking the binding of the ligand. Thus, the 1A5 antibody is herein referred to as a ligand-independent antibody. Increasing concentrations of 3D4 antibody inhibited binding of NRG1 to HER3 (FIG. 2A) indicating that the 3D4 antibody binds HER3 and blocks ligand binding. Thus, the 3D4 antibody is herein referred to as a ligand-dependent antibody. Flow cytometry was used to confirm these results. Briefly, HER3-transfected SP2/0 cells were incubated with 100 ng/ml of biotin-conjugated NRG1 in the absence or presence of increasing concentrations of 1A5 or 3D4. NRG1 binding was detected by PE-streptavidin. Increasing concentrations of the 1A5 antibody failed to block NRG1 binding to HER3; however, increasing concentrations of the 3D4 antibody blocked NRG1 binding to HER3 (FIG. 2B), thus, confirming the results of the ELISA assay.

Figure 3:
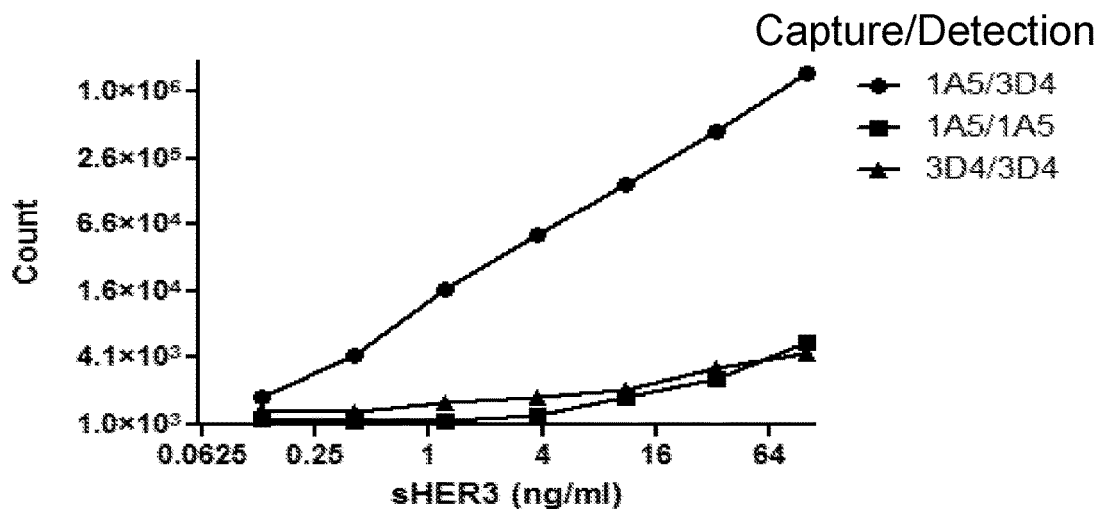
FIG. 3 shows a graph demonstrating that the 1A5 and 3D4 antibodies recognize different epitopes on HER3. An ELISA plate was coated with 2 μg/ml of purified 1A5 and then incubated with indicated concentrations of recombinant soluble HER3 in the presence of 200 ng/ml HRP-conjugated 3D4. The binding of 3D4 to HER3 was detected by chemiluminescence substrate. The average counts per second of triplicates are presented.
Figure 4A:
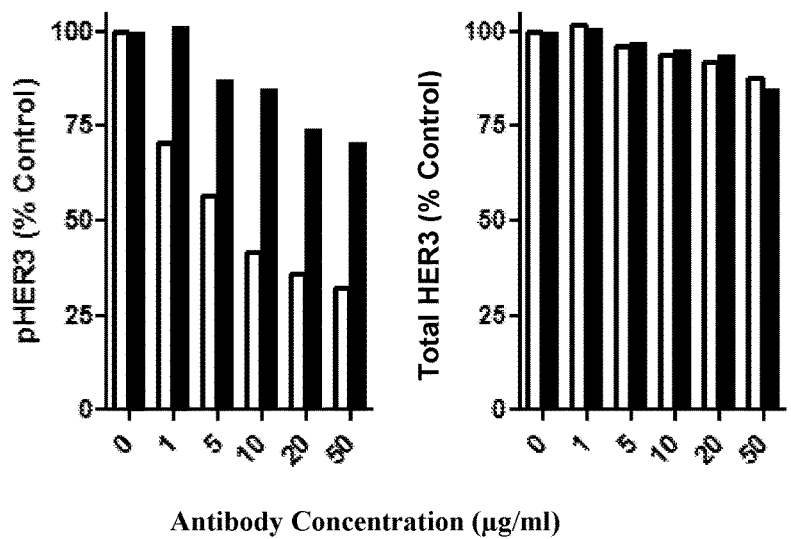
FIG. 4 shows in vitro dose-dependent inhibition of ligand-independent activation (autophosphorylation) of HER3 by the 1A5 antibody. Human gastric cancer N87 cells (FIG. 4A), breast cancer BT474 cells (FIG. 4B), breast cancer ZR75-30 cells (FIG. 4C), and pancreatic cancer Panc 2.03 cells (FIG. 4D) were treated with indicated concentrations of 1A5 or 3D4 antibodies for 24 hours. The tyrosine phosphorylation levels of HER3 (pHER3, left graph for FIGS. 4A-4D) were determined by ELISA in 2 mg/ml of total cell lysates. The ELISA plate was coated with 3F8 anti-HER3 antibody (recognizing a different epitope than 1A5 and 3D4) to capture total HER3 (Total HER3, right graph for FIGS. 4A-4D). The tyrosine-phosphorylated HER3 was detected by HRP-conjugated 4G10 anti-tyrosine phosphorylation antibody. The total HER3 was detected by HRP-conjugated 1E8 anti-HER3 antibody. The tyrosine-phosphorylated HER3 and total HER3 levels were then measured by chemiluminescence.
Figure 4B:
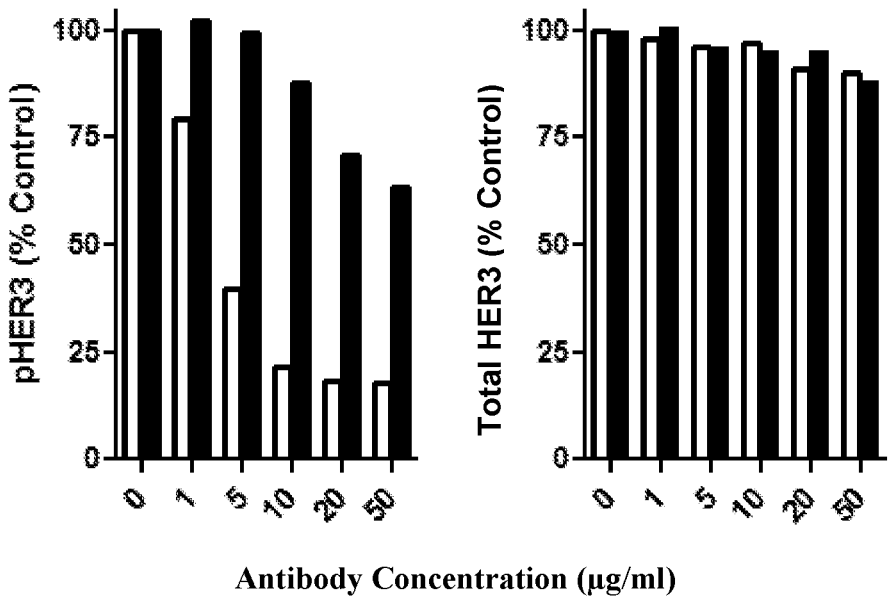
Figure 4C:
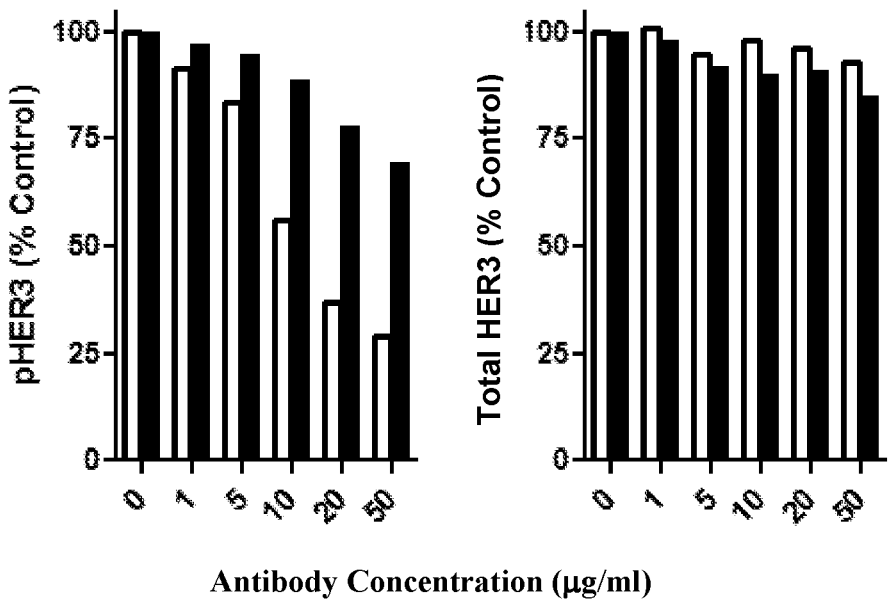
Figure 4D:
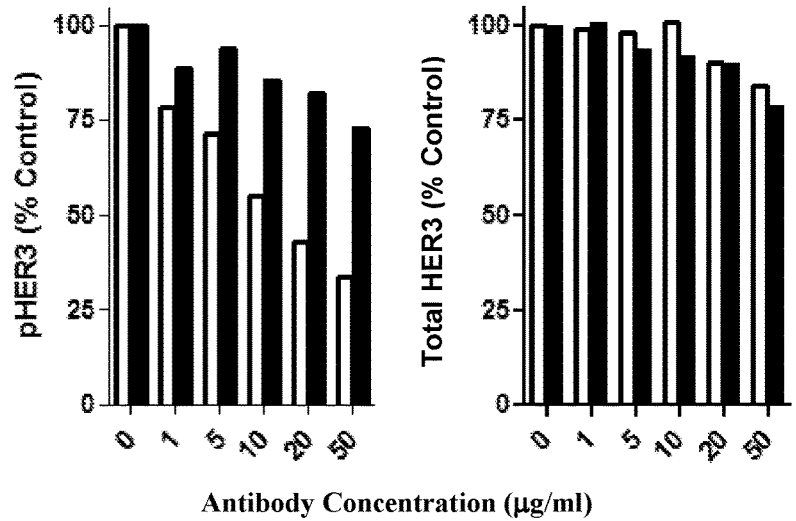

To determine if the 1A5 and 3D4 antibodies bind different epitopes of HER3, an ELISA assay was performed. An ELISA plate was coated with 2 µg/ml of purified 1A5 and then incubated with increasing concentrations of HER3 in the presence of 200 ng/ml HRP-conjugated 3D4. The binding of 3D4 antibody to HER3 was detected by chemiluminescence. It was determined that the 1A5 and 3D4 antibodies bind different epitopes of HER3 (FIG. 3).

To further characterize the antibodies, both the 1A5 and 3D4 antibodies were sequenced. Sequencing of the 1A5 antibody produced the following sequences: the variable region of the 1A5 heavy chain MEWIWIFLFIFSGTAGVH-SQVQLQQSGAELA RPGASVKLSCKASGYTFTDNY- INWMKQRPGQGLEWIGEIYPGSGNTYYNEKFKG-KATL TADKSSSTAYMQLSSLTSEESAVYFCARSPNLR-LYYFDYWGQGTTLTVSS (SEQ ID NO:1) and the variable region of the 1A5 light chain MVSTSQLLGLLLFWT SASRCDIVMTQSPATLSVTPGDRVSLSCRASQSINDY-LYWYQQKLHESPRLLIKFASHSIS GIPSRF-SGSGSGSDFTLSINSVEPEDVGVYYCQNGHSFPLTF-GAGTKLELK (SEQ ID NO:2). Further analysis of the variable region of the 1A5 light chain indicated a leader peptide consisting of MVSTSQLLGLLLFWTSASRC (SEQ ID NO:17); framework region 1 (FR1) of DIVMTQS-PATLSVTPGDRVSLSC (SEQ ID NO:18), FR2 of WYQQKLHESPRLLIK (SEQ ID NO:19), FR3 of GIPSRF-SGSGSGSDFTLSINSV EPEDVGVYYC (SEQ ID NO:20), FR4 of FGAGTKLELK (SEQ ID NO:21), complementarity determining region 1 (CDR1) of RASQSINDYLY (SEQ ID NO:3), CDR2 of FASHSIS (SEQ ID NO:4), and CDR3 of QNGHSFPLT (SEQ ID NO:5). Further analysis of the variable region of the 1A5 heavy chain a leader peptide consisting of MEWIWIFLFIFSGTAGVHS (SEQ ID NO:22); framework region 1 (FR1) of QVQLQQS-GAELARPGASVKLSCKASGYTFT (SEQ ID NO:23), FR2 of WMKQRPGQGLEWIG (SEQ ID NO:24), FR3 of KATLTADKSSSTAYMQLSSLTS EESAVYFCAR (SEQ ID NO:25), FR4 of WGQGTTLTVSS (SEQ ID NO:26), complementarity determining region 1 (CDR1) of DNYIN (SEQ ID NO:6), CDR2 of EIYPGSGNTYYNEKFKG (SEQ ID NO:7), and CDR3 of SPNLRLYYFDY (SEQ ID NO:8).

Sequencing of the 3D4 antibody produced the following sequences: the variable region of the 3D4 light chain MET-DTLLLWVLLLWVPGSTGDIVLTQSPASLAVSLG QRATISCRASESVDSYGNSFMNWYQQKPGQPPKVLI-YRASNLESGIPARFSGSGSRTDFT LTITPVEAD-DVATYYCQQSYEDPPTFGGGTKLEIK (SEQ ID NO:9) and the variable region of the 3D4 heavy chain MGWSRI-FLFLLSIIAGVHCQVQLQQSGPELV KPGASVRISCK-ASGYTFTNYFLHWMKQRPGQGLEWIGWIYPGN-VNTKYSEKFKGKATL TADKSSSTAYMQLSSLTSEDSAVYFCARSTYYSMDY-WGQGTSVTVSS (SEQ ID NO:10). Further analysis of the variable region of the 3D4 light chain indicated a leader peptide consisting of METDTLLLWVLLLWVPGSTG (SEQ ID NO:27); framework region 1 (FR1) of DIVLTQS-PASLAVSLGQRATISC (SEQ ID NO:28), FR2 of WYQQKPGQPPKVLIY (SEQ ID NO:29), FR3 of GIPARFSGSGSRTDFTLTIT PVEADDVATYYC(SEQ ID NO:30), FR4 of FGGGTKLEIK (SEQ ID NO:31), complementarity determining region 1 (CDR1) of RASESVDSYG-NSFMN (SEQ ID NO:11), CDR2 of RASNLES (SEQ ID NO:12), and CDR3 of QQSYEDPPT (SEQ ID NO:13). Further analysis of the variable region of the 3D5 heavy chain a leader peptide consisting of MGWSRIFLFLLSI-IAGVHC (SEQ ID NO:32); framework region 1 (FR1) of QVQLQQSGPELVKPGASVRISCKASGYTFT (SEQ ID NO:33), FR2 of WMKQRPGQGLEWIG (SEQ ID NO:34), FR3 of KATLTADKSSSTAYMQLSSL TSEDSAVYFCAR (SEQ ID NO:35), FR4 of WGQGTSVTVSS (SEQ ID NO:36), complementarity determining region 1 (CDR1) of NYFLH (SEQ ID NO:14), CDR2 of WIYPGNVNTKY-SEKFKG (SEQ ID NO:15), and CDR3 of STYYSMDY (SEQ ID NO:16).

Example 3

In Vitro Biological Function of the 1A5 and 3D4 Antibodies

Figure 5:
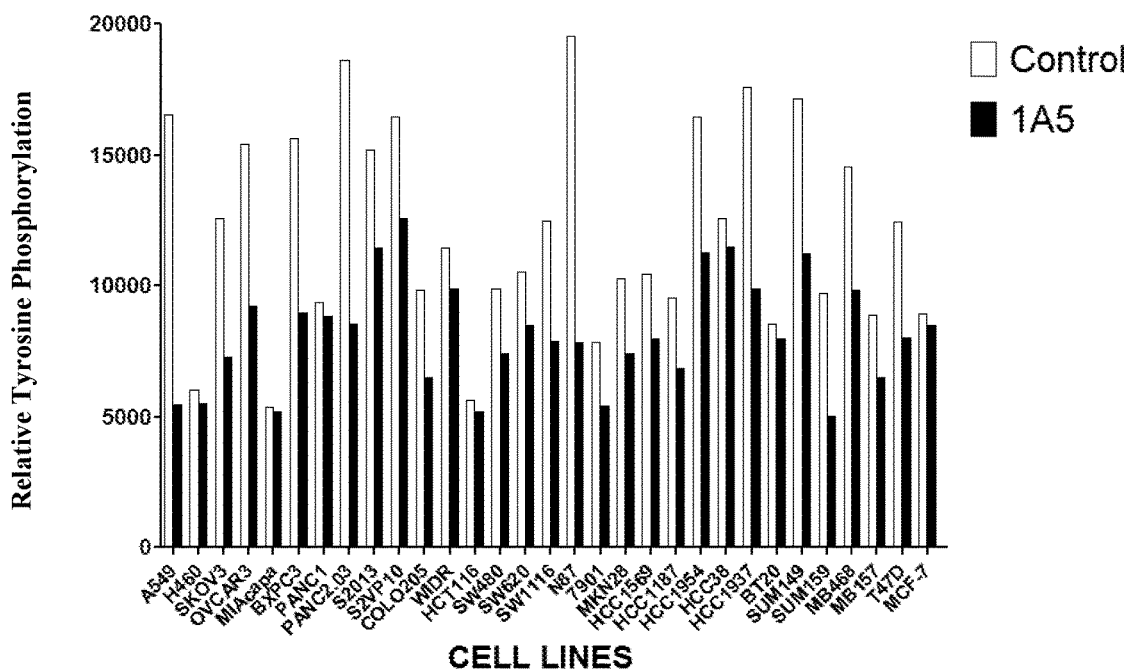
FIG. 5 shows the effect of 1A5 on autophosphorylation of a panel of human cancer cells. The cancer cells were treated with 20 μg/ml of the 1A5 antibody for 24 hours. The tyrosine-phosphorylation levels of HER3 were determined by ELISA in 2 mg/ml of total cell lysate. The ELISA plate was coated with 3F8 anti-HER3 antibody (recognizing a different epitope than the 1A5 antibody) to capture total HER3. The tyrosine-phosphorylated HER3 was detected by HRP-conjugated 4G10 anti-tyrosine phosphorylation antibody, and the levels of phosphorylation were measured by chemiluminescence.
Figure 6A:
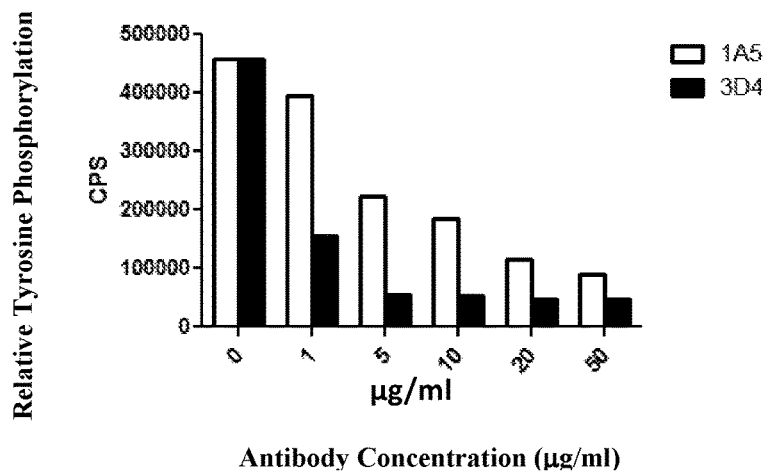
FIG. 6 shows a dose-dependent inhibition of ligand-dependent activation of HER3. Human gastric cancer N87 cells (FIG. 6A), breast cancer BT474 cells (FIG. 6B), breast cancer ZR75-30 cells (FIG. 6C), and pancreatic cancer Panc 2.03 cells (FIG. 6D) were treated with the indicated concentrations of 1A5 or 3D4 for 24 hours, and then treated with 100 pg/ml of recombinant NRG1 for one hour. The tyrosine phosphorylation levels of HER3 were determined by ELISA in 25 µl of 2 mg/ml total cell lysate. The ELISA plate was coated with 3F8 anti-HER3 antibody (recognizing a different epitope than 1A5 and 3D4) to capture total HER3. The tyrosine-phosphorylated HER3 was detected by HRP-conjugated 4G10 anti-tyrosine phosphorylation antibody, and the levels of phosphorylation were measured by chemiluminescence.
Figure 6B:
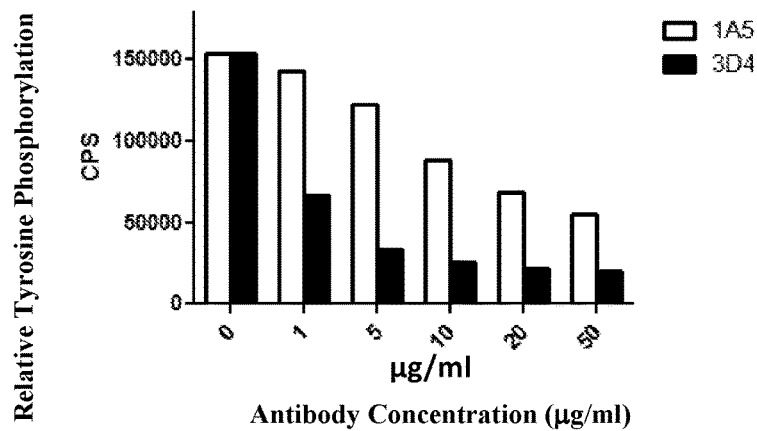
Figure 6C:
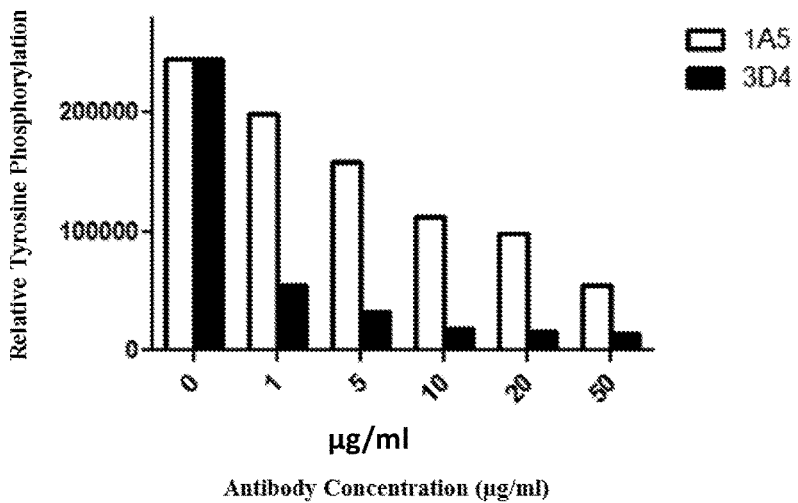
Figure 6D:
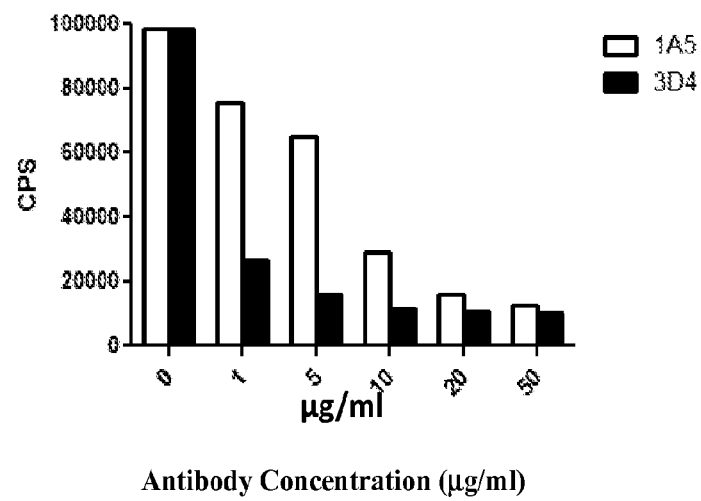
Figure 7A:
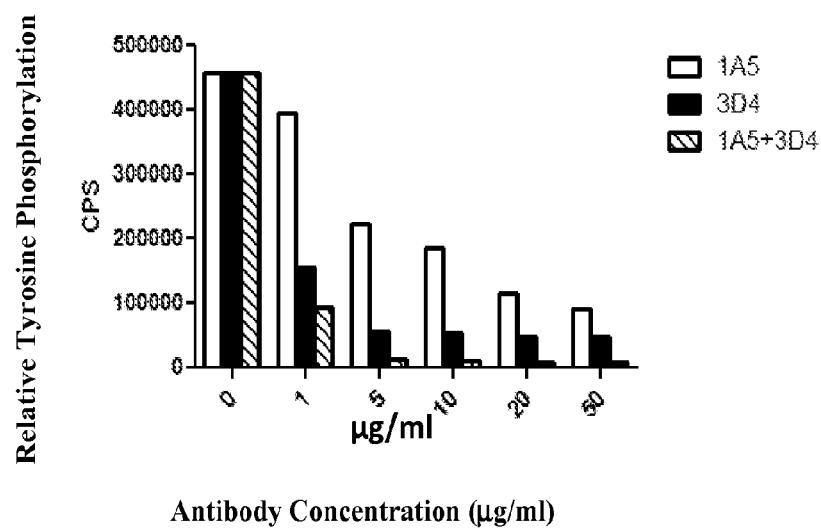
FIG. 7 shows the complete inactivation of HER3 by combination treatment with the 1A5 and 3D4 antibodies. Human gastric cancer N87 cells (FIG. 7A), breast cancer BT474 cells (FIG. 7B), breast cancer ZR75-30 cells (FIG. 7C), and pancreatic cancer Panc 2.03 cells (FIG. 7D) were treated with the indicated concentrations of 1A5 or 3D4 or both antibodies for 24 hours, and then the cells were treated with 100 pg/ml of recombinant NRG1 for one hour. The tyrosine phosphorylation levels of HER3 were determined by ELISA in 2 mg/ml of total cell lysate. The ELISA plate was coated with 3F8 anti-HER3 antibody (recognizing a different epitope than 1A5 and 3D4) to capture total HER3. The tyrosine-phosphorylated HER3 was detected by HRP-conjugated 4G10 anti-tyrosine phosphorylation antibody, and then the levels of phosphorylation were measured by chemiluminescence.
Figure 7B:
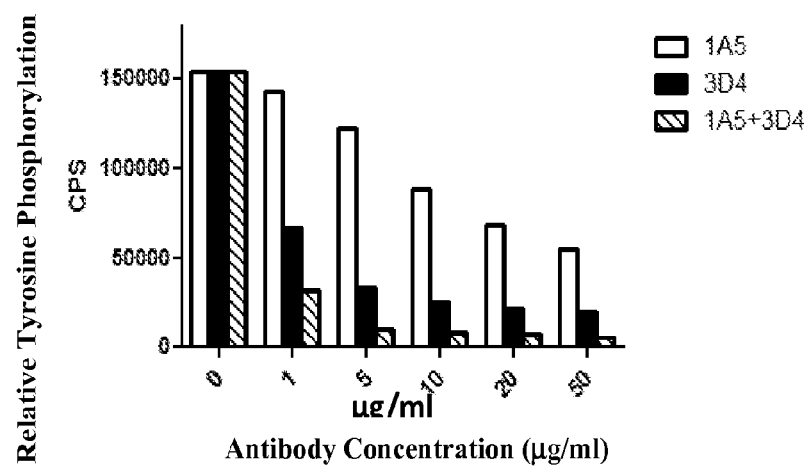
Figure 7C:
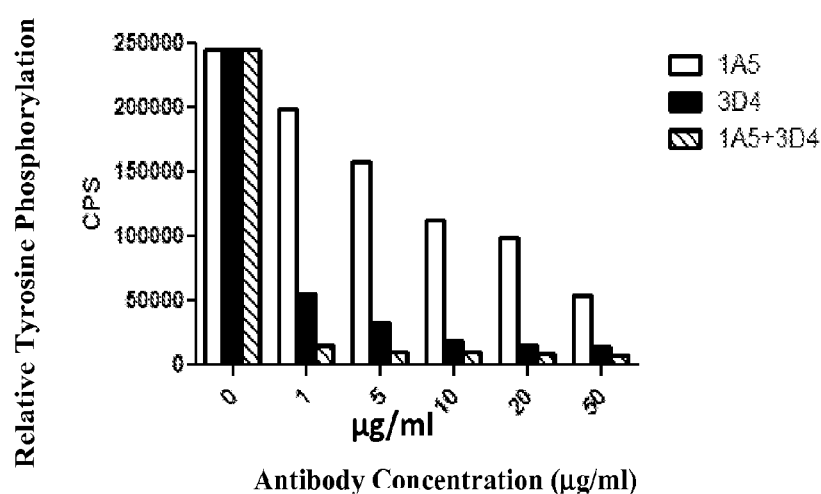
Figure 7D:
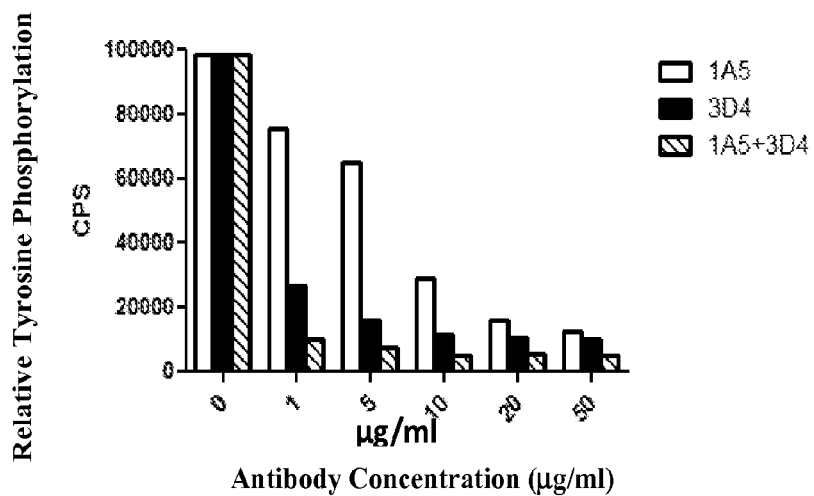

To determine whether the 1A5 antibody was capable of inhibiting ligand-independent activation (autophosphory-lation) of HER3, the 1A5 or 3D4 antibodies were administered to several cancer cell lines and autophosphorylation levels of HER3 were determined. Human gastric cancer N87 cells, breast cancer BT474 and ZR75-30 cells, and pancreatic cancer Panc 2.03 cells were treated with increasing concentrations of the 1A5 or 3D4 antibodies for 24 hours. The tyrosine phosphorylation levels of HER3 were determined using an ELISA assay in 2 mg/ml of total cell lysate. An ELISA plate was coated with 3F8 anti-HER3 antibody, which recognizes a different epitope than the 1A5 and 3D4 antibodies, to capture total HER3 (tHER3). Tyrosine phosphorylation levels were detected by chemiluminescence using an HRP-conjugated 4G10 anti-tyrosine phosphorylation antibody. It was determined that that increasing concentrations of the 1A5 antibody was capable of inhibiting autophosphorylation of HER3 to a greater extent than the ligand-dependent 3D4 antibody (FIGS. 4A-4D). FIG. 5 further shows the inhibition of ligand-independent activation of HER3 in a panel of human cancer cells lines. Tyrosine phosphorylation levels were determined by an ELISA assay in 2 mg/ml of total cell lysate, and the levels of tyrosine phosphorylation were detected by the HRP-conjugated 4G10 anti-tyrosine phosphorylation antibody.

To determine whether the 1A5 antibody was capable of inhibiting ligand-dependent activation of HER3, the 1A5 or 3D4 antibodies were administered in combination with recombinant NRG1 and tyrosine-phosphorylation levels of HER3 were determined. Human gastric cancer N87 cells, breast cancer BT474 and ZR75-30 cells, and pancreatic cancer Panc 2.03 cells were treated with increasing concentrations of the 1A5 or 3D4 antibodies for 24 hours, followed by administration of 100 pg/ml of recombinant NRG1 for 1 hour. The tyrosine phosphorylation levels of HER3 were determined using an ELISA assay in 25 µl of 2 mg/ml of total cell lysate. An ELISA plate was coated with 3F8 anti-HER3 antibody to capture total HER3. Tyrosine phosphorylation levels were detected by chemiluminescence using an HRP-conjugated 4G10 anti-tyrosine phosphorylation antibody. It was determined that that increasing concentrations of the 1A5 antibody was capable of inhibiting ligand-dependent activation of HER3 to a lesser extent than the ligand-dependent 3D4 antibody (FIGS. 6A-6D).

To determine whether administration of the 1A5 and 3D4 antibodies in combination would have a synergistic effect on inhibiting activation of HER3, the antibodies were administered in combination to the cell lines and tyrosine-phosphorylation levels of HER3 were determined, as described above. It was determined that the antibodies synergistically act together to inhibit activation of HER3 when administered in combination at low concentrations (FIGS. 7A-7D).

Figure 8A:
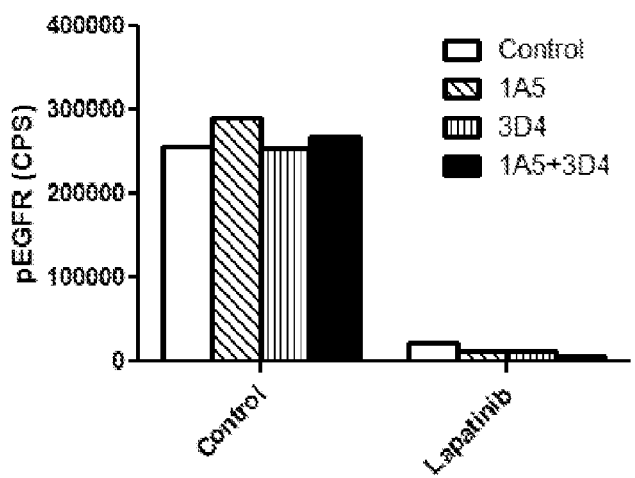
FIG. 8 shows that the complete blockade of HER3 activation with the 1A5 and 3D4 antibodies sensitizes the anti-proliferation effect of lapatinib in N87 gastric cancer cells. Human gastric cancer N87 cells were treated with 20 µg/ml 1A5 or 3D4 or both with or without 100 nM lapatinib for 24 hours. The tyrosine phosphorylation levels of EGFR (FIG. 8A), HER2 (FIG. 8B) and HER3 (FIG. 8C) were determined by chemiluminescence ELISA in 2 mg/ml of total cell lysates. The ELISA plate was coated with anti-EGFR (clone: 1E1, FIG. 8A), anti-HER2 (clone: 5G12, FIG. 8B), or anti-HER3 (clone: 3F8, FIG. 8C). The tyrosine-phosphorylated EGFR, HER2, and GER3 were detected by HRP-conjugated 4G10 anti-tyrosine phosphorylation antibody, and the levels of phosphorylation were measured by chemiluminescence. Cells were labeled with EdU, and the EdU+ proliferating cells were examined by flow cytometry (FIG. 8D).
Figure 8B:
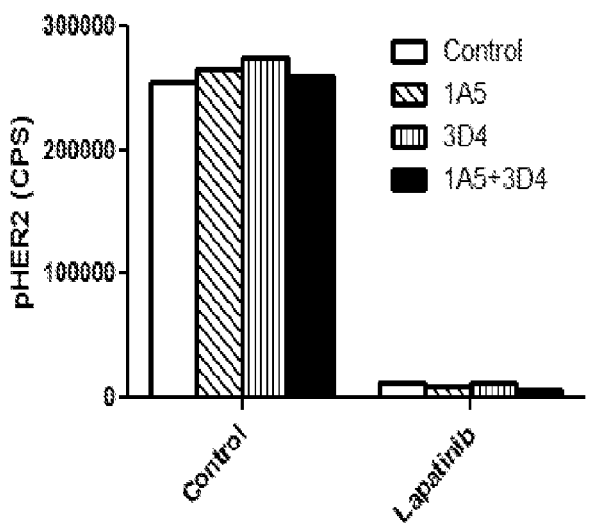
Figure 8C:
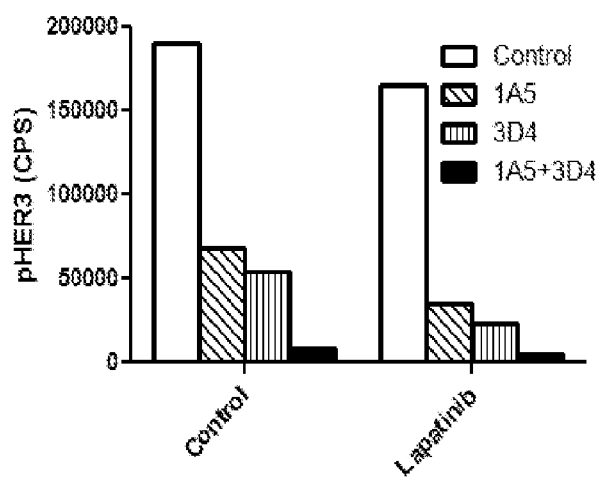
Figure 8D:
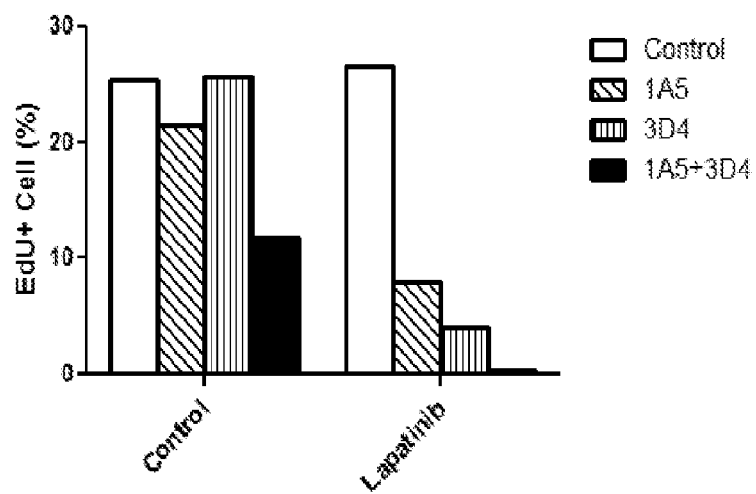

To determine whether administration of the 1A5 and 3D4 antibodies in combination with lapatanib would affect the proliferation of N87 gastric cancer cell lines, the 1A5 and 3D4 antibodies, alone and in combination, were administered to the N87 cells with or without lapatinib and tyrosine-phosphorylation levels of HER3 were determined. The human gastric cancer N87 cells were treated with 20 mg/ml of the 1A5 or 3D4 or both antibodies with or without 100 nM lapatinib for 24 hours. Tyrosine-phosphorylation levels of EGFR (FIG. 8A), HER2 (FIG. 8B), and HER3 (FIG. 8C) were determined by chemiluminescence. An ELISA plate was coated with anti-EGFR (clone: 1E1), anti-HER2 (clone: 5G12), and anti-HER3 (clone: 3F8), and tyrosine-phosphorylation levels were determined with the HRP-conjugated 4G10 anti-tyrosine phosphorylation antibody. It was determined that treatment with the 1A5 or 3D4 antibody, alone or in combination, did not affect the level of tyrosine phosphorylation for EGFR or HER2 (FIGS. 8A and 8B). The EGFR and HER2 tyrosine phosphorylation levels were reduced by administration of lapatinib with the antibodies (FIGS. 8A and 8B). Administration of 1A5 or 3D4 or both antibodies reduced the tyrosine phosphorylation of HER3 (FIG. 8C), and this effect was enhanced with the administration of lapatinib (FIG. 8C). To determine the effect of cell proliferation after administration of 1A5 or 3D4 or both antibodies with or without lapatinib, a cell proliferation assay was employed. Cells were labeled with EdU, and the EdU+ proliferating cells were detected by flow cytometry. It was observed that administration of both antibodies with lapatinib completely inhibited cell proliferation (FIG. 8D).

Figure 9A:
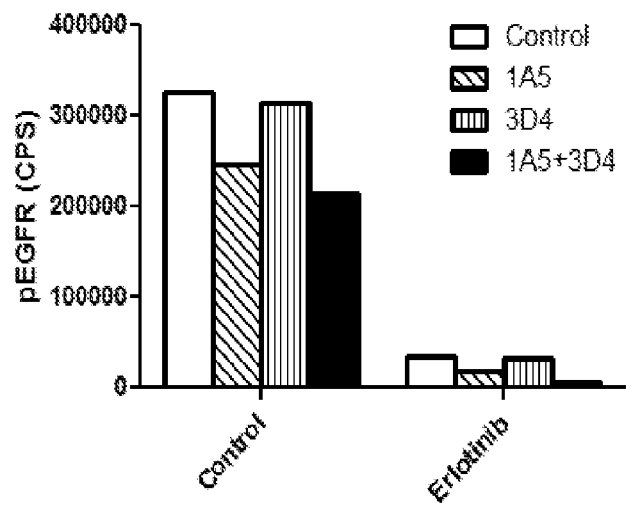
FIG. 9 shows that the complete blockade of HER3 activation with the 1A5 and 3D4 antibodies sensitizes the anti-proliferation effect of Erlotinib in A549 lung cancer cells. Human lung cancer A549 cells were treated with 20 µg/ml of 1A5 or 3D4 or both with or without 100 nM Erlotinib for 24 hours. The tyrosine phosphorylation levels of EGFR (FIG. 9A) and HER3 (FIG. 9B) were determined by chemiluminescence ELISA in 2 mg/ml of total cell lysate. The ELISA plate was coated with anti-EGFR (clone: 1E1, FIG. 9A) or anti-HER3 (clone: 3F8, FIG. 9B). The tyrosine-phosphorylated EGFR and HER3 was detected by HRP-conjugated 4G10 anti-tyrosine phosphorylation antibody, and the levels of phosphorylation were measured by chemiluminescence. Cells were labeled with EdU, and the EdU+ proliferating cells were examined by flow cytometry (FIG. 9C).
Figure 9B:
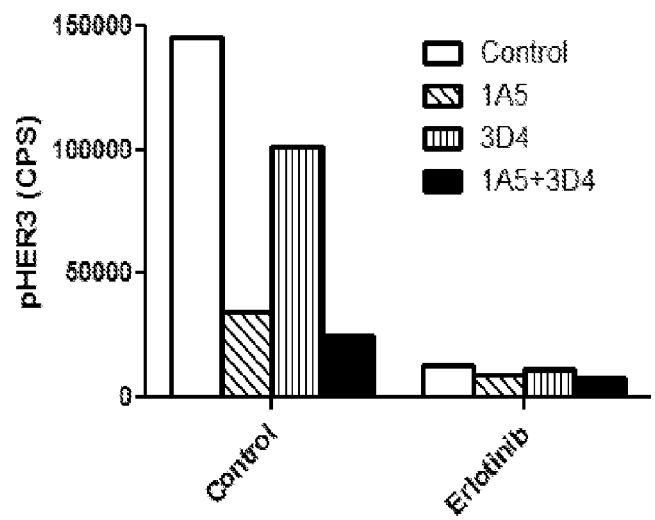
Figure 9C:
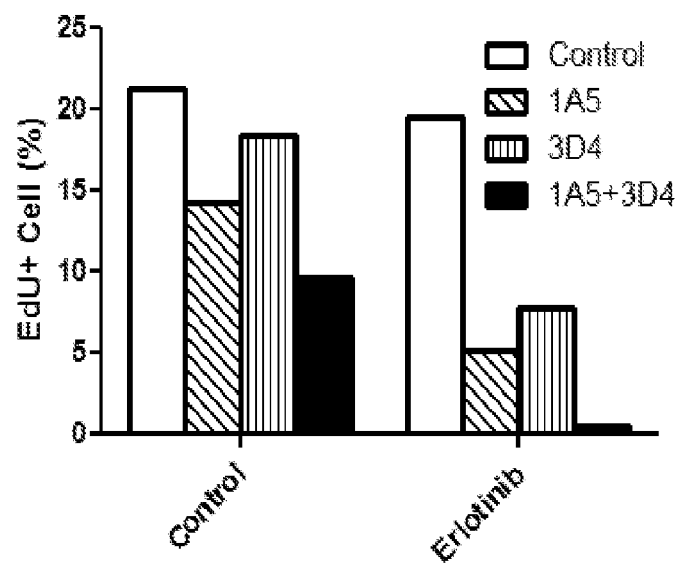

These experiments were repeated with A549 lung cancer cells with the drug Erlotinib. It was shown that administration of 1A5 or 3D4 or both antibodies did not affect tyrosine phosphorylation levels of EGFR (FIG. 9A), while administration of the antibodies with Erlotinib reduced tyrosine-phosphorylation levels of EGFR (FIG. 9A). Administration of 1A5 or 3D4 or both antibodies reduced the tyrosine-phosphorylation levels of HER3, and this effect was enhanced administering Erlotinib in combination with the antibodies, alone and in combination (FIG. 9B). Using flow cytometry, it was observed that administration of both antibodies with Erlotinib completely inhibited cell proliferation of the A549 lung cancer cells (FIG. 9C).

Figure 10A:
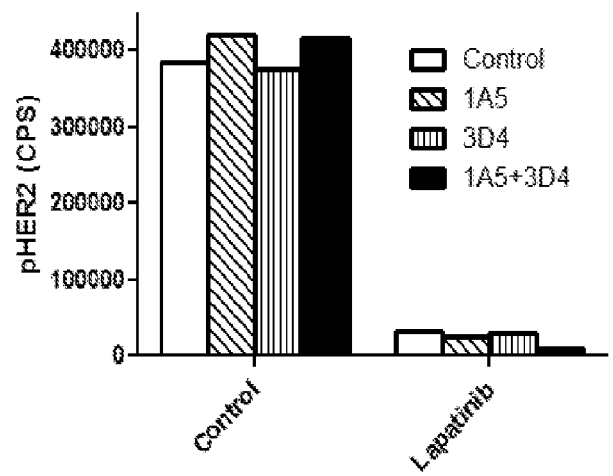
FIG. 10 shows that the complete blockade of HER3 activation with the 1A5 and 3D4 antibodies sensitizes the anti-proliferation effect of lapatinib in ZR75-30 breast cancer cells. Human breast cancer ZR75-30 cells were treated with 20 µg/ml of 1A5 or 3D4 or both antibodies with or without 100 nM lapatinib for 24 hours. The tyrosine phosphorylation levels of HER2 (FIG. 10A) and HER3 (FIG. 10B) were determined by chemiluminescence ELISA in 2 mg/ml of total cell lysate. The ELISA plate was coated with anti-HER2 (clone: 5G12) or anti-HER3 (clone: 3F8). The tyrosine-phosphorylated HER2 and HER3 was detected by HRP-conjugated 4G10 anti-tyrosine phosphorylation antibody, and the levels of phosphorylation were measured by chemiluminescence. Cells were labeled with EdU, and the EdU+ proliferating cells were examined by flow cytometry (FIG. 10C).
Figure 10B:
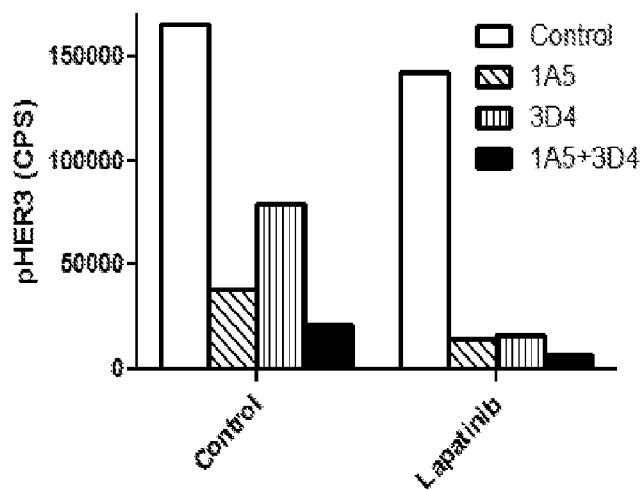
Figure 10C:
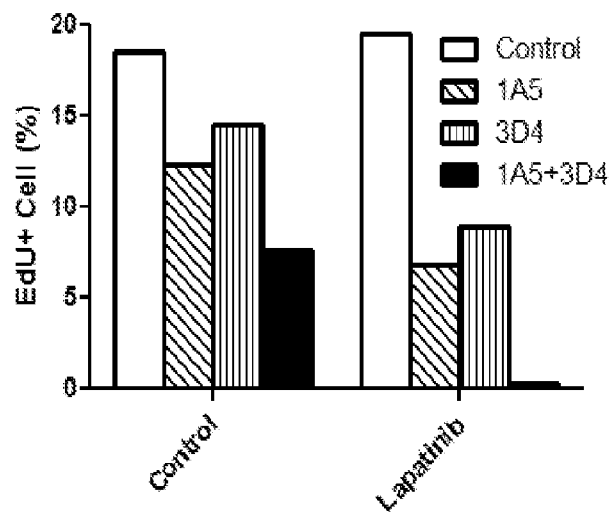

These experiments were repeated with ZR75-30 breast cancer cells and lapatinib. Administration of 1A5 or 3D4 or both antibodies did not affect tyrosine phosphorylation levels of HER2 (FIG. 10A); however, the administration of lapatinib with the antibodies alone or in combination reduced tyrosine phosphorylation levels (FIG. 10A). Administration of 1A5 or 3D4 or both antibodies reduced the tyrosine phosphorylation levels of HER3, and this effect was enhanced with the administration of lapatinib with the antibodies, alone and in combination (FIG. 10B). Using flow cytometry, it was observed that administration of both antibodies with lapatinib completely inhibited cell proliferation of the ZR75-30 breast cancer cells (FIG. 10C).

Example 4

In Vivo Anti-Tumor Efficacy of the 1A5 and 3D4 Antibodies

Figure 11:
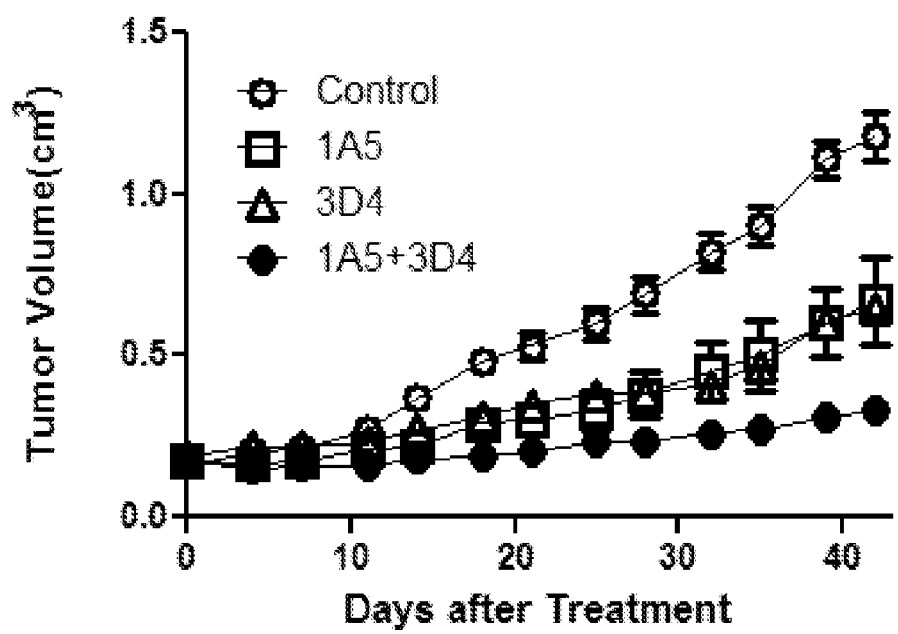
FIG. 11 shows a graph demonstrating the blockade of HER3 activation with the 1A5 and 3D4 antibodies reduces tumor volume in an A549 human lung cancer xenograft model.
Figure 12:
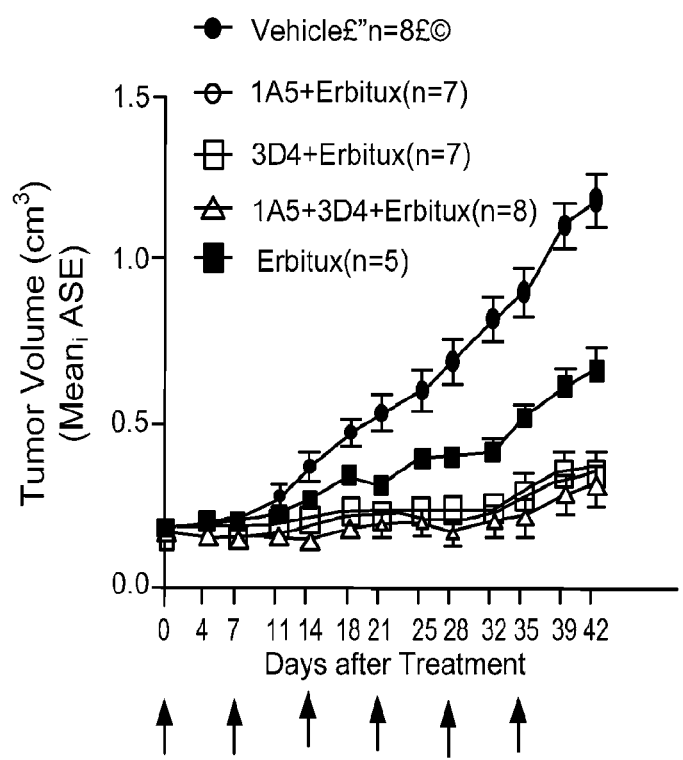
FIG. 12 shows a graph demonstrating the blockade of HER3 activation with the 1A5 and 3D4 antibodies in combination with Erbitux synergistically reduces tumor volume in an A549 human lung cancer xenograft model.

To determine whether the 1A5 antibody was capable on inhibiting tumor growth in vivo, different cancer xenograft models were used. Using the A549 human lung cancer xeongraft model, it was shown that administration of the 1A5 or 3D4 antibody alone reduced tumor volume (FIG. 11). Further, administration of the 1A5 and 3D4 antibodies in combination demonstrated that the antibodies could synergistically reduce tumor volume in the A549 human lung cancer xeongraft model. Using the same model, it was demonstrated that administration of Erbitux with the 1A5 or 3D4 antibodies, alone and in combination, reduced tumor volume more than administration of Erbitux alone (FIG. 12).

Figure 13:
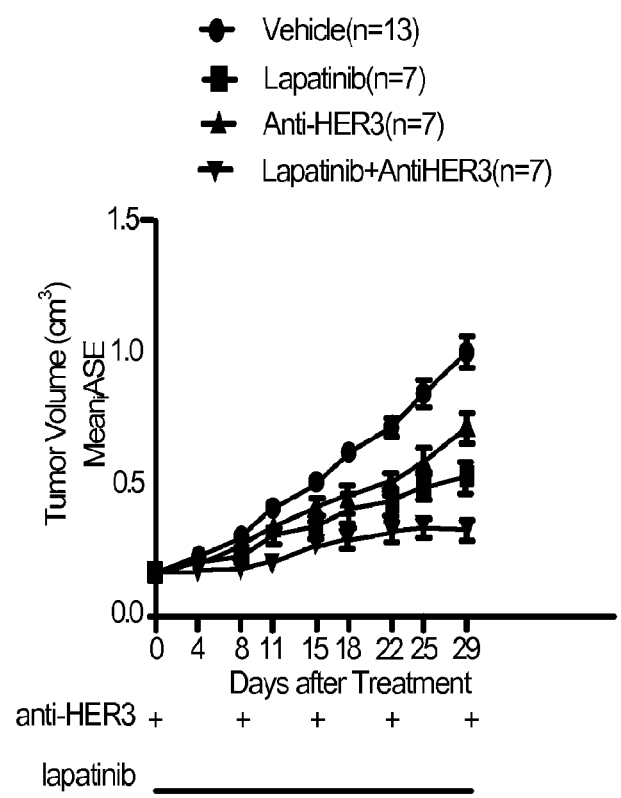
FIG. 13 shows a graph demonstrating the blockage of HER3 activation with the 1A5 antibody in combination with lapatinib synergistically reduces tumor volume in a N87 human gastric cancer model.

Using the N87 human gastric cancer xenograft model, it was demonstrated that administration of lapatinib reduced tumor volume more than the administration of the combination of 1A5 and 3D4 antibodies (anti-HER3); however, administration of lapatinib in combination with both antibodies showed the greatest reduction in tumor volume (FIG. 13).

Figure 14:
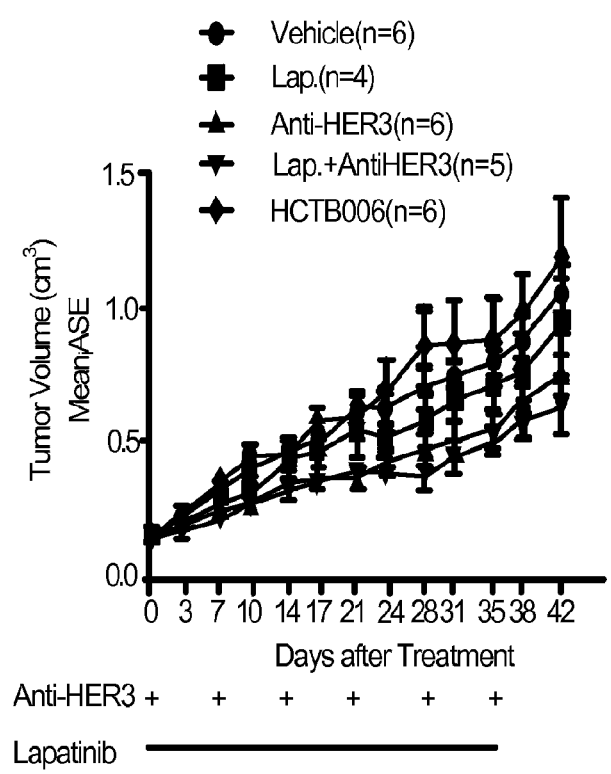
FIG. 14 shows a graph demonstrating the blockade of HER3 activation with the 1A5 antibody in combination with lapatinib synergistically reduces tumor volume in a MKN28 human gastric cancer model.

Using the MKN28 human gastric cancer xenograft model, it was demonstrated that administration of the combination of 1A5 and 3D4 antibodies (anti-HER3) had a greater tumor volume reducing effect than administration of lapatinib alone (FIG. 14). Administration of lapatinib in combination with both antibodies showed the greatest reduction in tumor volume (FIG. 14).

Figure 15:
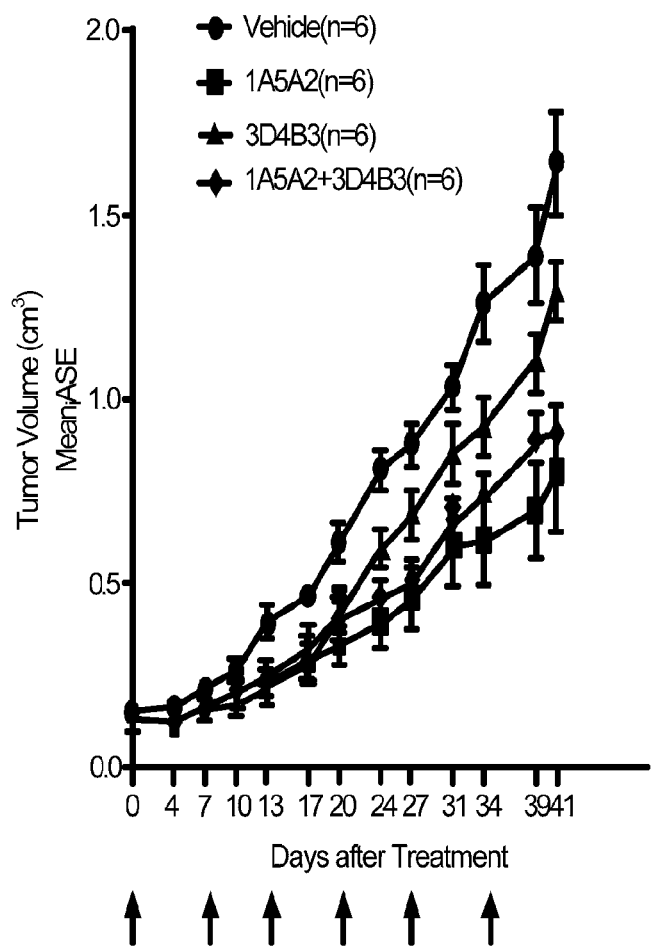
FIG. 15 shows a graph demonstrating the blockade of HER3 activation with the 1A5 antibody reduces tumor volume in a HT29 human colon cancer model.
Figure 16:
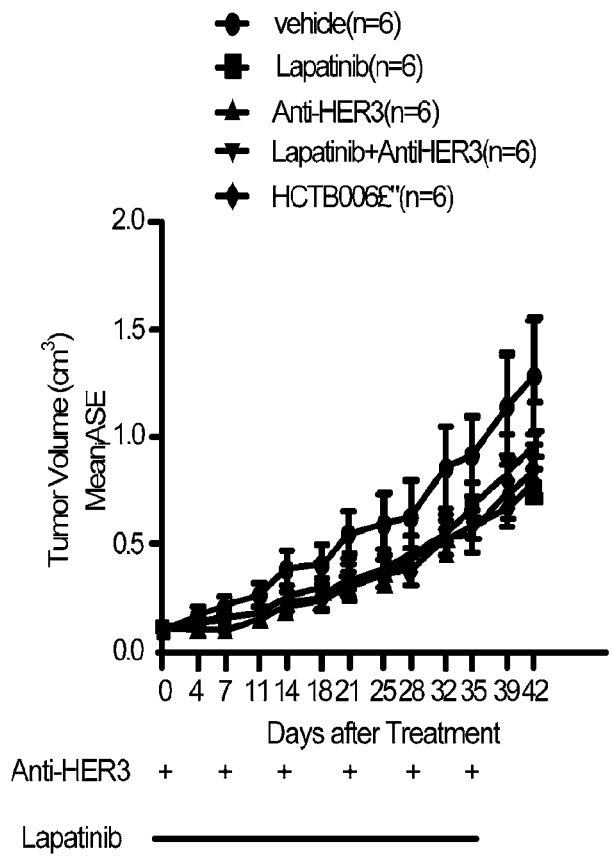
FIG. 16 shows a graph demonstrating the blockade of HER3 activation with the 1A5 antibody in combination with lapatinib synergistically reduces tumor volume in a HT29 human colon cancer model.

Using the HT29 human colon cancer xenograft model, it was demonstrated that the administration of the 1A5 antibody alone had the greatest tumor volume reducing effect than the administration of the 3D4 antibody or the administration of the 1A5 and 3D4 antibodies in combination (FIG. 15). Administration of the antibodies in combination with lapatinib, the antibodies in combination, and lapatinib alone resulted in similar reductions in tumor volume in the same HT29 human colon cancer xenograft model (FIG. 16).

Example 5

Figure 17A:
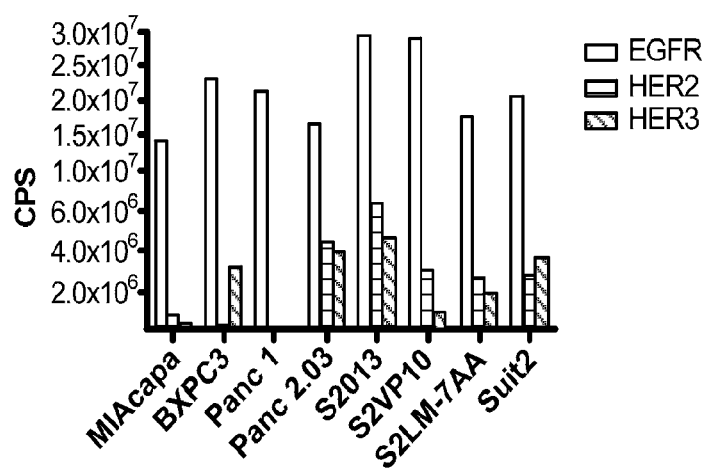
FIG. 17A shows all cell lines expressed high levels of EGFR and five and seven out of eight cell lines expressed variable levels of HER2 and HER3, respectively.
Figure 17B:
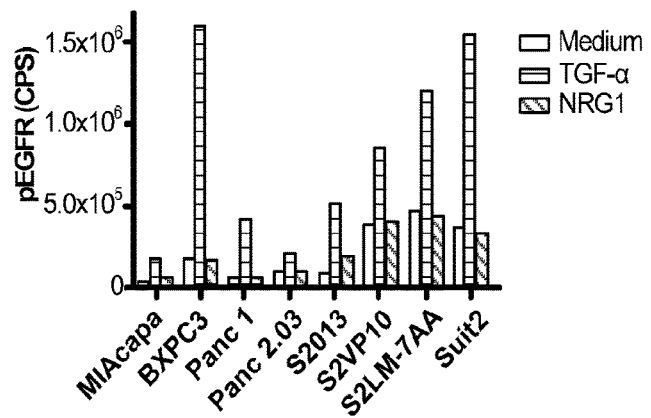
FIGS. 17B-17D show TGF-α induced a differential phosphorylation response independent of EGFR expression levels, but did not activate HER2 and HER3. NRG1 did not induce EGFR activation but was able to activate both HER2 and HER3 in a HER-dependent fashion. All HER3 positive cell lines had different levels of HER3 autophosphorylation (ligand-independent activation).
Figure 17C:
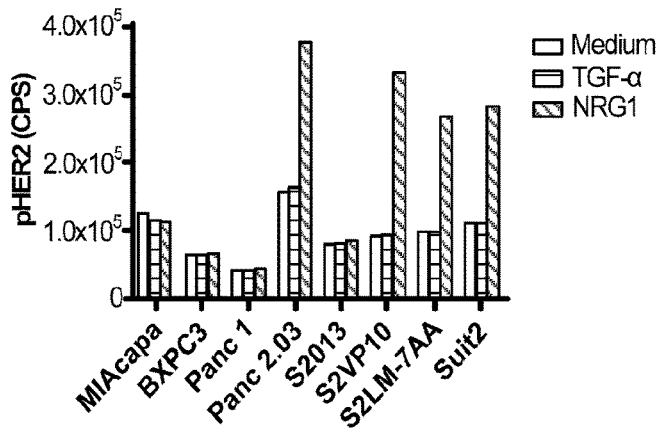
Figure 17D:
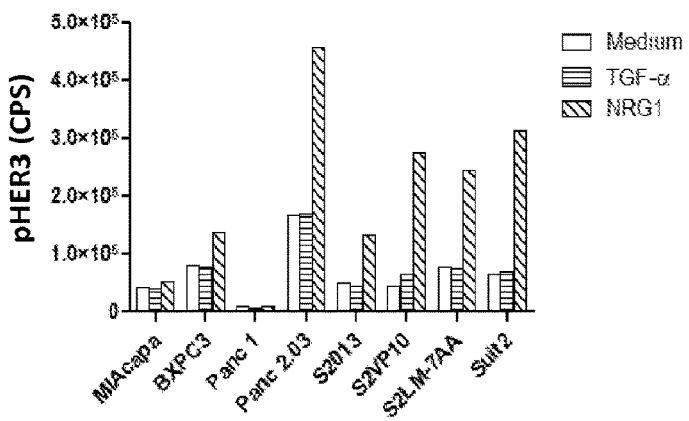

In Vitro Biological Function of 1A5 and 3D4 Antibodies on Pancreatic Cancer Cell Lines The effects of the 1A5 and 3D4 antibodies were investigated in several pancreatic cell lines. The cell lines were first tested to determine the expression and function of ERBB family proteins. All cell lines expressed high levels of EGFR, 5 out of 8 cell lines expressed variable levels of HER2, and 7 out of 8 cell lines expressed variable levels of HER3 (FIG. 17A). TGF-α induced a differential phosphorylation response independent of EGFR expression levels but did not activate HER2 or HER3 (FIGS. 17B-17D). NRG1 did not induce EGFR activation, but was able to activate both HER2 and HER3 in a HER3-dependent fashion. All HER3 positive cell lines had different levels of HER3 autophosphorylation (FIGS. 17B-17D).

Figure 18A:
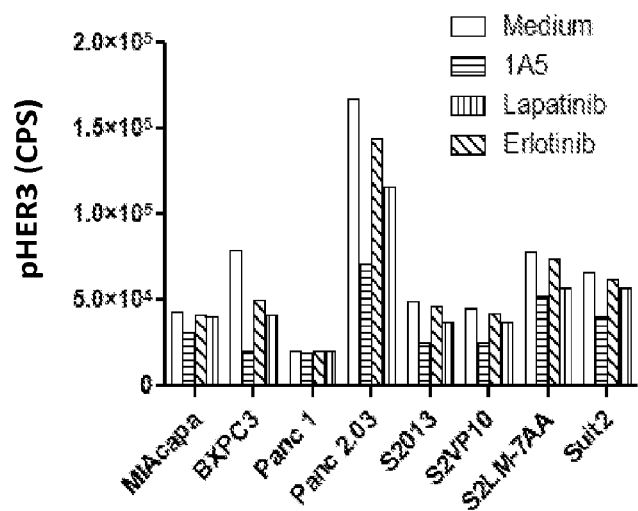
FIG. 18A shows that the 1A5 antibody but not erlotinib and lapatinib inhibited autophosphorylation of HER3 in all HER3 positive cell lines, except Panc 1.
Figure 18B:
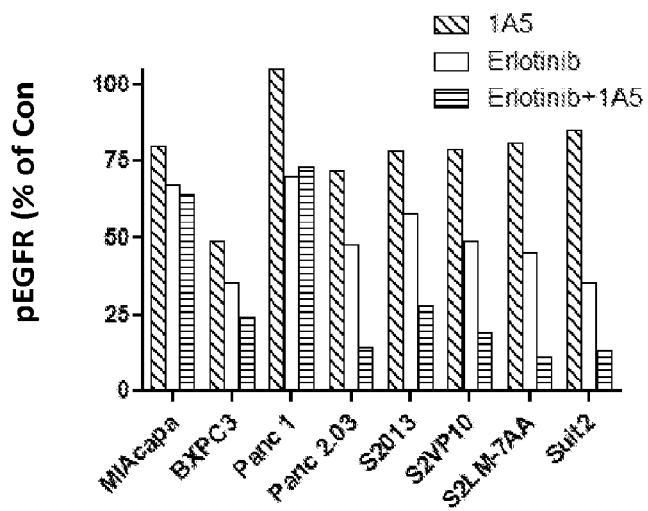
FIG. 18B shows that erlotinib inhibited autophosphorylation in all pancreatic cell lines, while the 1A5 antibody alone partially inhibited EGFR autophosphorylation in a HER3-dependent fashion. The 1A5 antibody was able to enhance the inhibitory activity of erlotinib.
Figure 18C:
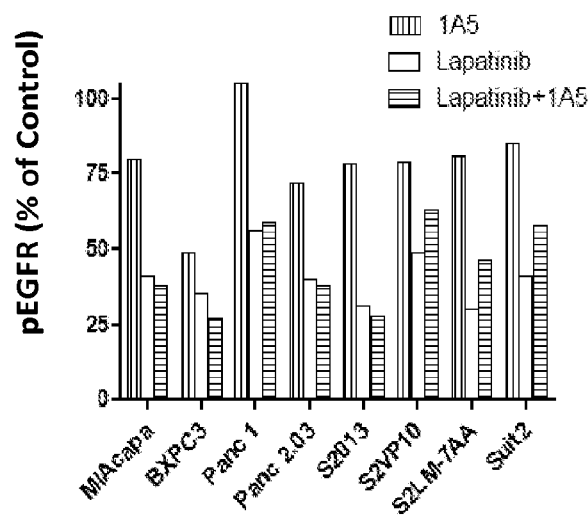
FIG. 18C shows lapatinib alone inhibited autophosphorylation of EGFR; however, the 1A5 antibody was not able to enhance the activity of lapatinib.
Figure 18D:
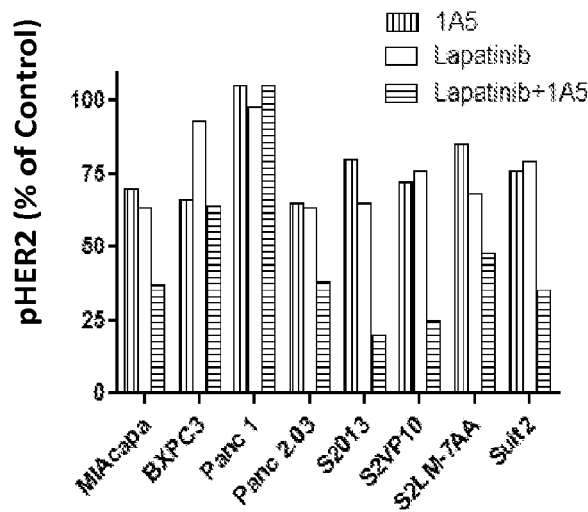
FIG. 18D shows the combination of 1A5 and lapatinib reduced the levels of HER2 autophosphorylation to a greater extent than the 1A5 antibody or lapatinib alone.

Using the pancreatic cancer cell lines, the effect of the 1A5 antibody on autophosphorylation of EGFR, HER2, and HER3 was investigated. The 1A5 antibody but not erlotinib and lapatinib inhibited autophosphorylation of HER3 in all HER3 positive cell lines except for Panc1 (FIG. 18A). Erlotinib inhibited autophosphorylation of EGFR in all pancreatic cell lines, while the 1A5 antibody alone partially inhibited EGFR autophosphorylation in a HER3-dependent fashion (FIG. 18B). The 1A5 antibody was capable of enhancing the inhibitory activity of erlotinib in reducing autophosphorylation of EGFR (FIG. 18B). Lapatinib alone inhibited autophosphorylation of EGFR; however, the 1A5 antibody was not able to enhance the activity of lapatinib (FIG. 18C). The 1A5 antibody or lapatinib alone partially inhibited autophosphorylation of HER2; however, the combination of the 1A5 antibody and lapatinib significantly reduced levels of HER2 autophosphorylation.

Figure 19A:
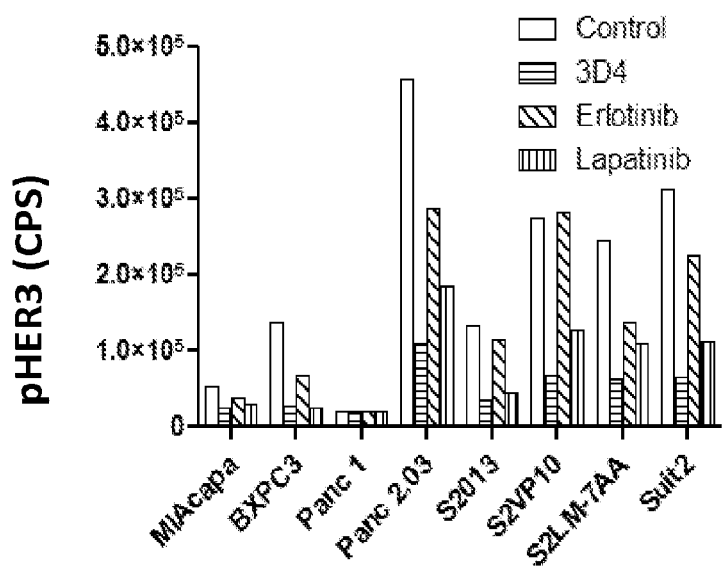
FIG. 19A shows that the 3D4 antibody inhibited NRG-1 induced phosphorylation of HER3 and lapatinib partially reduced NRG-1-induced phosphorylation.
Figure 19B:
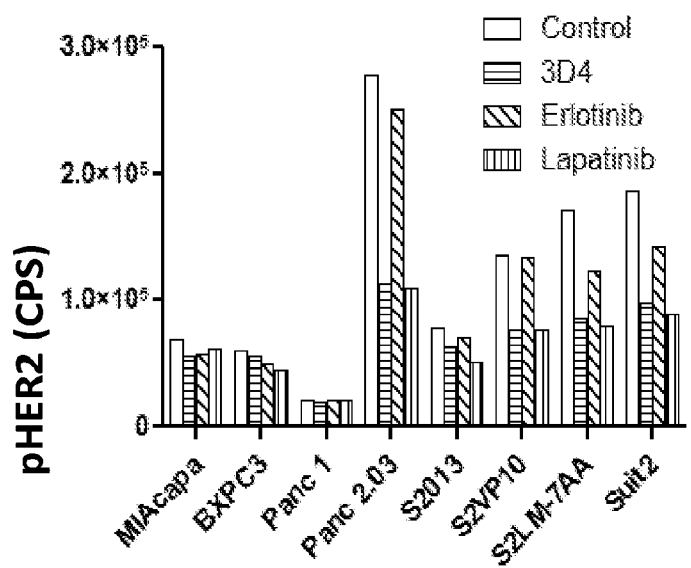
FIG. 19B shows that both the 3D4 antibody and lapatinib, but not erlotinib, inhibited NRG-1-induced phosphorylation of HER2.
Figure 20A:
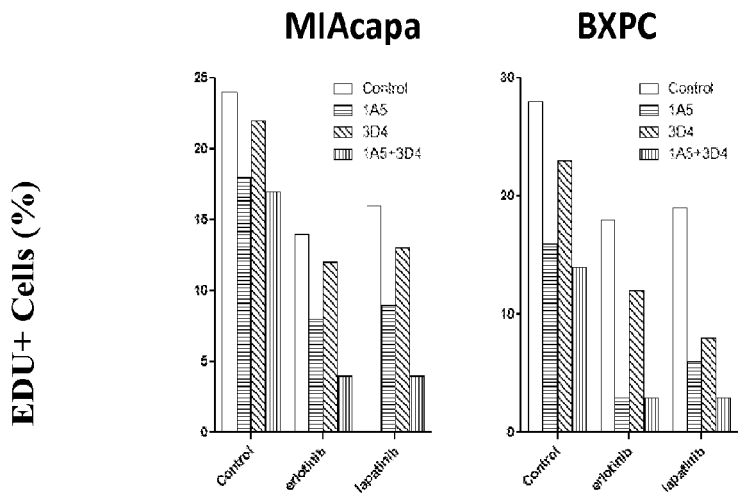
FIG. 20A shows the anti-proliferation activity of a combination treatment with the anti-HER3 antibodies and erlotinib or lapatinib in the MIAcapa (left) and BXPC3 (right) cell lines.
Figure 20B:
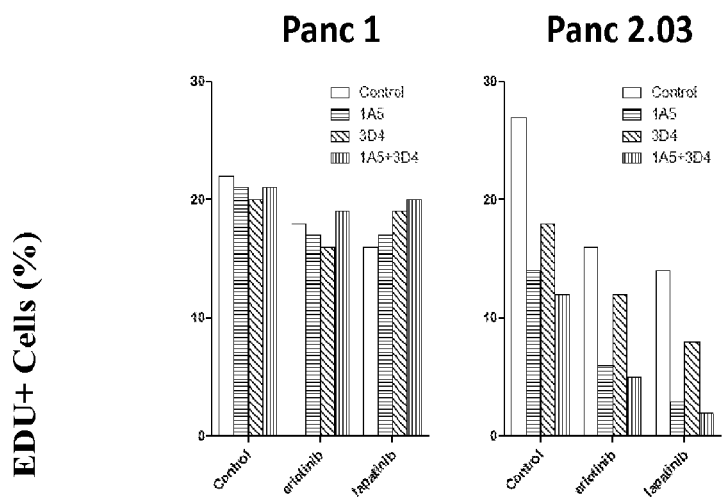
FIG. 20B shows the anti-proliferation activity of a combination treatment with the anti-HER3 antibodies and erlotinib or lapatinib in the Panc1 (left) and Panc 2.03 (right) cell lines.
Figure 20C:
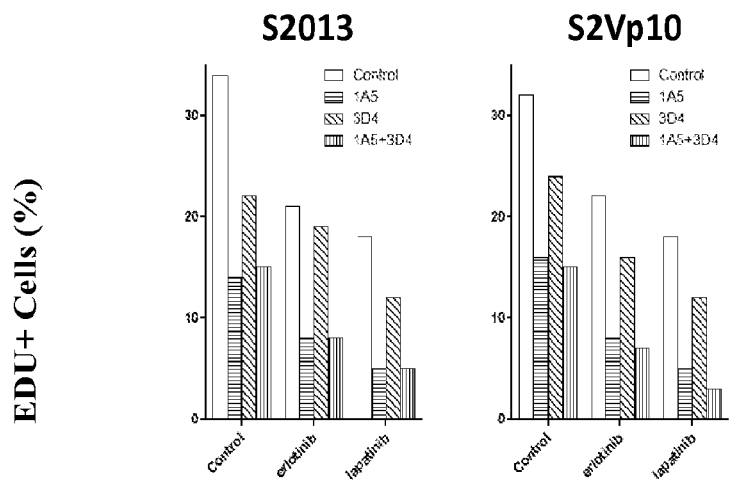
FIG. 20C shows the anti-proliferation activity of a combination treatment with the anti-HER3 antibodies and erlotinib or lapatinib in the S2013 (left) and S2Vp10 (right) cell lines.
Figure 20D:
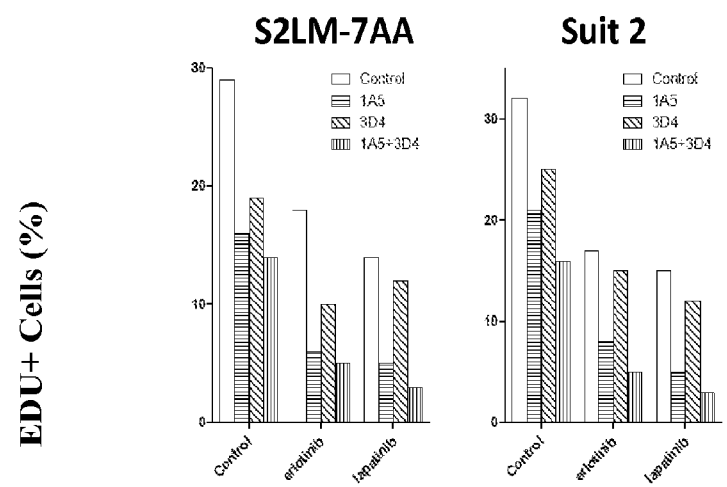
FIG. 20D shows the anti-proliferation activity of a combination treatment with the anti-HER3 antibodies and erlotinib or lapatinib in the S2LM-7AA (left) and Suit 2 (right) cell lines.

Using the pancreatic cancer cell lines, the effect of the 3D4 antibody on ligand-dependent activation of HER3 and HER2 was also investigated. It was shown that the 3D4 antibody inhibited NRG1-induced phosphorylation of HER3, while lapatinib only partially inhibited NRG1-induced phosphorylation of HER3 (FIG. 19A). It was further shown that both the 3D4 antibody and lapatinib, but not erlotinib, inhibited NRG1-induced phosphorylation of HER2.

Using the pancreatic cancer cell lines, the anti-proliferative effect of the 1A5 antibody, 3D4 antibody, or the 1A5 and 3D4 antibodies in combination with erlotinib or lapatnib was investigated. It was shown that the 1A5 and 3DR4 antibodies in combination with erlotinib and lapatinib significantly reduced proliferation of the pancreatic cancer cell lines, with the exception of the Panc1 cell line (FIGS. 20A-20D).

Example 6

Figure 21:
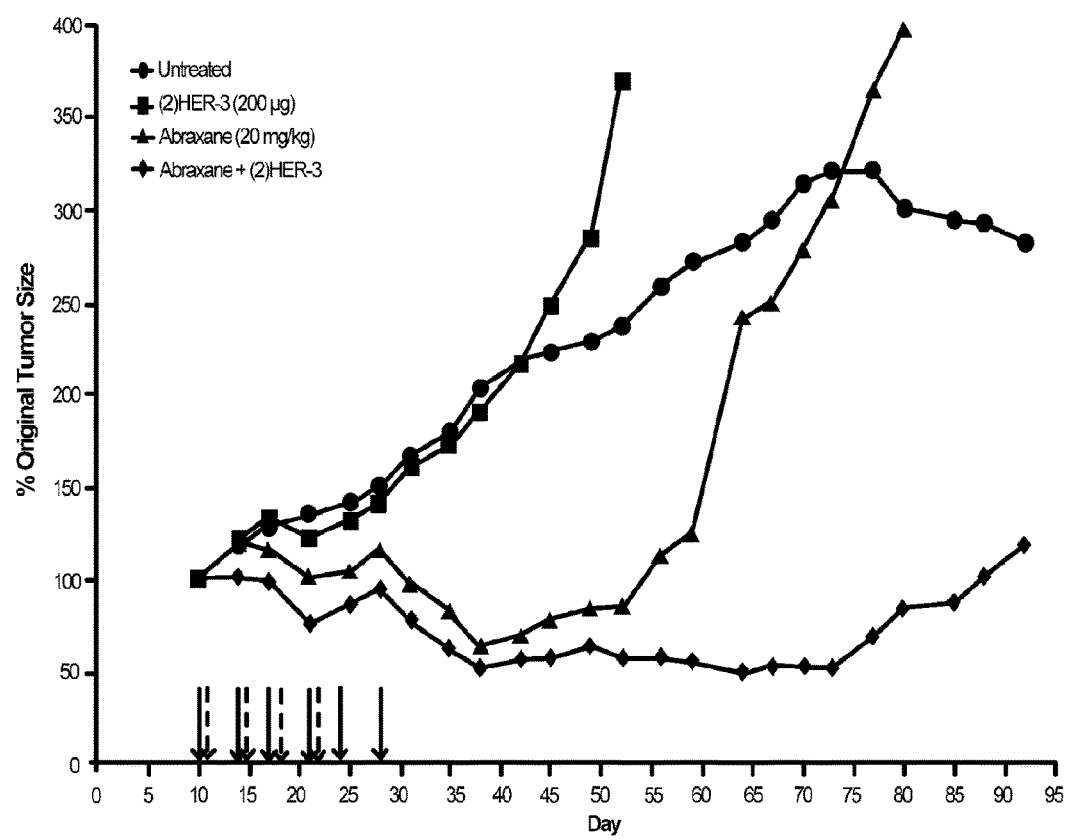
FIG. 21 shows in vivo efficacy of HER3 antibodies alone and in combination with Abraxane against orthotopic basal A xenografts in athymic nude mice. HCC1187 cells were implanted in the mammary fat pad, and treatments began 10 days later when tumors were well established. The arrows indicate the interval during which treatment was administered (n=10 mice/group). Treatment consisted of 200 µg 1A5 and 3D4 HER3 antibodies given twice a week for 3 weeks ending on day 28, 20 mg/kg Abraxane on days 11, 15, 18, and 22, HER3 plus Abraxane, or no treatment.
Figure 22:
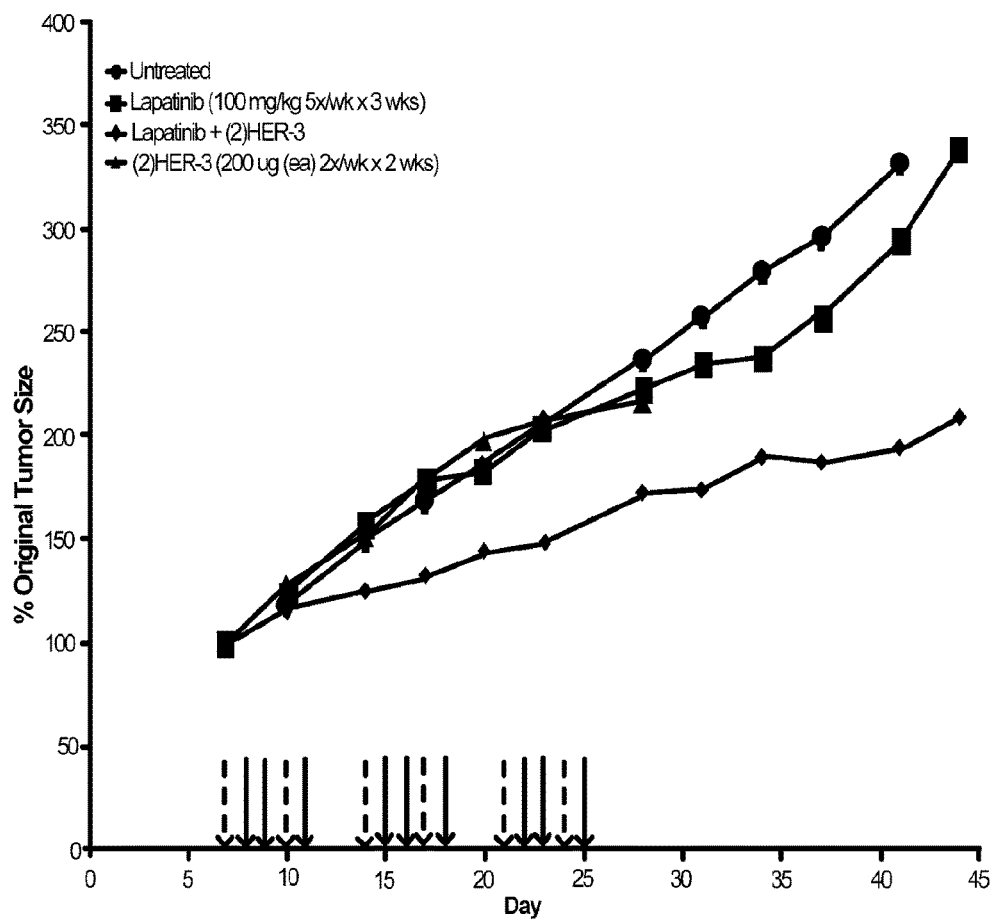
FIG. 22 shows in vivo efficacy of HER3 antibodies alone and in combination with Lapatinib against orthotopic basal A xenografts in athymic nude mice. MDA-MB-468 cells were implanted in the mammary fat pad, and treatments began 7 days later when tumors were well established. The arrows indicate the interval during which treatment was administered (n=10 mice/group). Treatment consisted of 200 µg 1A5 and 3D4 HER3 antibodies given twice a week for 3 weeks ending on day 24, 100 mg/kg Lapatinib 5 days a week for 3 weeks, HER3 plus Lapatinib, or no treatment.
Figure 23:
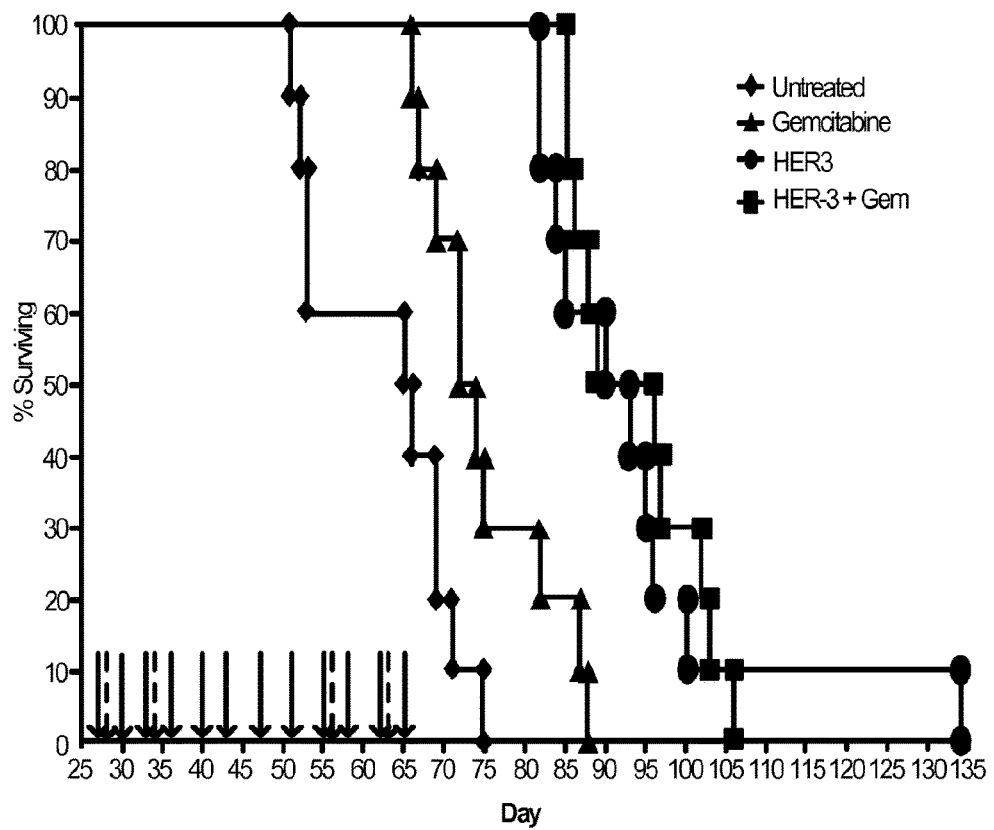
FIG. 23 shows in vivo efficacy of HER3 antibodies alone and in combination with Gemcitabine against orthotopic pancreatic cancer xenografts in athymic nude mice. MIA PaCa-2 cells were implanted in the pancreas, and treatments began 27 days later when tumors were well established. The arrows indicate the interval during which treatment was administered (n=10 mice/group). Treatment consisted of 200 µg 1A5 and 3D4 HER3 antibodies given twice a week for 6 weeks ending on day 65, 120 mg/kg Gemcitabine on days 28, 34, 56, and 63, HER3 plus Gemcitabine, or no treatment.

In Vitro Biological Function of 1A5 and 3D4 Antibodies on Breast Cancer and Pancreatic Cancer The effects of the 1A5 and 3D4 antibodies were investigated in in vivo models of breast cancer and pancreatic cancer. In these studies, breast cancer and pancreatic cancer orthotopic xenografts were treated with a cycle of therapy consisting of an equal mixture of the 1A5 ligand-independent HER3 antibody and the 3D4 ligand dependent HER3 antibody alone or in combination with chemotherapeutic agents or a tyrosine kinase inhibitor (Abraxane or lapatinib for breast cancer, gemcitabine for pancreatic cancer). Unexpectedly, HER3 antibodies alone produced no inhibition of the HCC1187 basal A breast cancer xenografts, while Abraxane produced growth inhibition. Also surprising was that HER3 antibodies in combination with Abraxane (FIG. 21) or lapatinib (FIG. 22) produced prolonged tumor growth inhibition of HCC1187 and MDA-MB-468 basal A xenografts. The third unexpected finding was that the HER3 antibodies alone or in combination with gemcitabine produced an equal enhancement in survival of mice bearing MIA PaCa-2 human pancreatic orthotopic tumor xenografts compared to gemcitabine or no treatment (FIG. 23).

---

What is claimed is:

1. An antibody specific for HER3, wherein the antibody does not block ligand binding and wherein the antibody blocks phosphorylation of HER3, wherein the antibody comprises a light chain with polypeptide sequences comprising SEQ ID NO:3, SEQ ID NO:4, and SEQ ID NO:5 and a heavy chain with polypeptide sequences comprising SEQ ID NO:6, SEQ ID NO:7, and SEQ ID NO:8.

2. The antibody of claim 1, wherein the phosphorylation is independent of ligand binding to HER3.

3. The antibody of claim 1, wherein the antibody at low doses in vitro blocks phosphorylation of HER3 in a cancer cell expressing HER3.

4. The antibody of claim 1, wherein the antibody sensitizes blocking phosphorylation of HER2 and EGFR.

5. The antibody of claim 1 wherein the light chain comprises SEQ ID NO: 2 and the heavy chain comprises SEQ ID NO: 1.

6. A method of treating cancer in a subject comprising administering to the subject an effective amount of the antibody of claim 1.

7. The method of claim 6, wherein the subject is selected as having a HER3 expressing cancer.

8. The method of claim 6, further comprising administering to the subject an antibody that blocks ligand binding to HER3.

9. The method of claim 6, further comprising administering to the subject an antibody that blocks ligand binding to HER2.

10. The method of claim 6, further comprising administering to the subject one or more chemotherapeutic agents.

11. The method of claim 6, further comprising administering to the subject an antibody that blocks ligand binding to EGFR.

12. The method of claim 6, further comprising administering to the subject one or more tyrosine kinase inhibitors.

13. The method of claim 12, wherein the one or more tyrosine kinase inhibitors are selected from the group consisting of Erlotinib and Lapatinib.

14. A method of reducing resistance to a tyrosine kinase inhibitor in a subject, comprising administering to the subject the HER3 antibody of claim 1.

15. The method of claim 14, further comprising administering to the subject an antibody that blocks HER3 ligand binding.

16. A method of reducing resistance to a chemotherapeutic agent in a subject, comprising administering to the subject the HER3 antibody of claim 1.

17. The method of claim 16, further comprising administering to the subject an antibody that blocks HER3 ligand binding.

* * * * *

UNITED STATES PATENT AND TRADEMARK OFFICE
CERTIFICATE OF CORRECTION

Page 1 of 1

PATENT NO. : 9,637,543 B2
APPLICATION NO. : 14/357524
DATED : May 2, 2017
INVENTOR(S) : Tong Zhou et al.

It is certified that error appears in the above-identified patent and that said Letters Patent is hereby corrected as shown below:

In the Specification

Column 1, Lines 13-15, Delete:
"This invention was made with government funding under Grant No. RO1-CA112169 from the National Institutes of Health. The government has certain rights in this invention."
And Insert:
-- This invention was made with government support under grant numbers CA112169, CA123197 and CA101955 awarded by the National Institutes of Health. The government has certain rights in the invention. --

Signed and Sealed this
First Day of October, 2019

Andrei Iancu
*Director of the United States Patent and Trademark Office*